US011571437B2

(12) United States Patent
Quinn et al.

(10) Patent No.: US 11,571,437 B2
(45) Date of Patent: Feb. 7, 2023

(54) METHODS OF TREATING CANCER USING PRMT5 INHIBITORS

(71) Applicant: Janssen Pharmaceutica NV, Beerse (BE)

(72) Inventors: Hillary Joy Millar Quinn, Perkiomenville, PA (US); Kathryn Elizabeth Packman, Newton, MA (US); Nahor Haddish-Berhane, Doylestown, PA (US); Geert S. J. Mannens, Lier (BE); Junguo Zhou, Flemington, NJ (US); Anthony T. Greway, Bound Brook, NJ (US); Dirk Brehmer, Freiburg (DE); Yue Guo, North Wales, PA (US); Tongfei Wu, Hever (BE); Hong Xie, Dresher, PA (US); Josh Lauring, Towson, MD (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/893,477

(22) Filed: Jun. 5, 2020

(65) Prior Publication Data
US 2020/0384006 A1 Dec. 10, 2020

Related U.S. Application Data

(60) Provisional application No. 62/858,076, filed on Jun. 6, 2019.

(30) Foreign Application Priority Data

Aug. 27, 2019 (EP) .................... 19193850

(51) Int. Cl.
A61K 31/7064 (2006.01)
A61P 35/04 (2006.01)
A61K 9/00 (2006.01)

(52) U.S. Cl.
CPC .......... *A61K 31/7064* (2013.01); *A61P 35/04* (2018.01); *A61K 9/0019* (2013.01); *A61K 9/0053* (2013.01)

(58) Field of Classification Search
CPC ................................. A61K 31/7064
See application file for complete search history.

(56) References Cited

U.S. PATENT DOCUMENTS

| 4,224,438 | A | 9/1980 | Fauland et al. |
| 6,143,749 | A | 11/2000 | Bhagwat et al. |
| 9,856,218 | B2 * | 1/2018 | Baiocchi ............. C07D 209/88 |
| 10,653,711 | B2 | 5/2020 | Wu et al. |
| 11,059,850 | B2 | 7/2021 | Verhoeven et al. |
| 2003/0225205 | A1 | 12/2003 | Epple et al. |
| 2003/0232783 | A1 | 12/2003 | Ibrahim et al. |
| 2004/0043959 | A1 | 3/2004 | Bloom et al. |
| 2005/0209176 | A1 | 9/2005 | Meutermans et al. |
| 2006/0167241 | A1 | 7/2006 | Hayakawa |
| 2008/0132525 | A1 | 6/2008 | Wahhab et al. |
| 2011/0159111 | A1 | 6/2011 | Curry et al. |
| 2012/0035115 | A1 | 2/2012 | Manoharan et al. |
| 2013/0023491 | A1 | 1/2013 | Annes et al. |
| 2013/0310333 | A1 | 11/2013 | Chesworth et al. |
| 2013/0310334 | A1 | 11/2013 | Chesworth et al. |
| 2014/0100184 | A1 | 4/2014 | Song et al. |
| 2014/0213582 | A1 | 7/2014 | Duncan et al. |
| 2014/0221345 | A1 | 8/2014 | Duncan et al. |
| 2014/0228343 | A1 | 8/2014 | Duncan et al. |
| 2014/0329794 | A1 | 11/2014 | Duncan et al. |
| 2016/0009744 | A1 | 1/2016 | Duffey et al. |
| 2016/0244475 | A1 | 8/2016 | Tatlock et al. |
| 2017/0198006 | A1 | 7/2017 | Duncan et al. |

(Continued)

FOREIGN PATENT DOCUMENTS

| JP | 2005-527502 A | 9/2005 |
| JP | 2006-503020 A | 1/2006 |

(Continued)

OTHER PUBLICATIONS

Brehmer, Dirk et al., Experimental and Molecular Therapeutics, "Abstract DDT02-04: A novel PRMT5 inhibitor with potent in vitro and in vivo activity in preclinical lung cancer models", Jul. 2017, AACR Annual Meeting (Year: 2017).*
Gerhart, Sarah et al., Supplemental Data, 98 pages, corresponding to Scientific Reports article (Scientific Reports, Jun. 2018, vol. 8, 15 pages, cited in IDS submitted Nov. 13, 2020). (Year: 2018).*
Reagan-Shaw, Shannon et al., The FASEB Journal, "Dose translation from animal to human studies revisited", 2007, vol. 22, pp. 659-661 (Year: 2007).*

(Continued)

*Primary Examiner* — Bahar Craigo
(74) *Attorney, Agent, or Firm* — BakerHostetler

(57) ABSTRACT

The present disclosure provides methods for treating a human patient diagnosed with a cancer, comprising administering a therapeutically effective amount of a PRMT5 (protein arginine methyltransferase 5) inhibitor, certain methods comprising (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 21 days; and (ii) administering to the patient subsequent doses of at least about 0.1 mg per day of the PRMT5 inhibitor for one or more subsequent dosing periods of about 5 to about 21 days each. In these methods, a first subsequent dosing period is separated in time from the initial dosing period by at least about 5 days and the subsequent dosing periods are separated in time from each other by at least about 5 days.

42 Claims, 4 Drawing Sheets

(56) References Cited

U.S. PATENT DOCUMENTS

| | | |
|---|---|---|
| 2018/0243328 A1 | 8/2018 | Wu et al. |
| 2019/0263833 A1 | 8/2019 | Wu et al. |
| 2020/0010881 A1 | 1/2020 | Brehmer et al. |
| 2020/0360416 A1 | 11/2020 | Wu et al. |

FOREIGN PATENT DOCUMENTS

| | | |
|---|---|---|
| JP | 2016-505001 A | 2/2016 |
| TW | I730980 B | 6/2021 |
| WO | WO 1996/040686 A1 | 12/1996 |
| WO | WO 2003/039523 A3 | 5/2003 |
| WO | WO 2003/070739 A1 | 8/2003 |
| WO | WO 2003/074083 A1 | 9/2003 |
| WO | 2004/022572 A1 | 3/2004 |
| WO | WO 2005/065150 A2 | 7/2005 |
| WO | WO 2005/065150 A3 | 7/2005 |
| WO | WO 2006/078752 A2 | 7/2006 |
| WO | WO 2006/078752 A3 | 7/2006 |
| WO | WO 2010/039548 A2 | 4/2010 |
| WO | WO 2010/039548 A3 | 4/2010 |
| WO | WO 2011/075665 A2 | 6/2011 |
| WO | WO 2011/075665 A3 | 6/2011 |
| WO | WO 2012/075500 A2 | 6/2012 |
| WO | WO 2012/075500 A3 | 6/2012 |
| WO | WO 2012/082436 A2 | 6/2012 |
| WO | WO 2012/082436 A3 | 6/2012 |
| WO | WO 2012/083170 A1 | 6/2012 |
| WO | WO 2012/138530 A1 | 10/2012 |
| WO | WO 2013/151975 A1 | 10/2013 |
| WO | WO 2014/035140 A2 | 3/2014 |
| WO | WO 2014/035140 A3 | 3/2014 |
| WO | WO 2014/100695 A1 | 6/2014 |
| WO | WO 2014/100719 A2 | 6/2014 |
| WO | WO 2014/100719 A3 | 6/2014 |
| WO | WO 2014/100730 A1 | 6/2014 |
| WO | WO 2015/106025 A1 | 7/2015 |
| WO | WO 2015/200680 A3 | 12/2015 |
| WO | WO 2015/200680 A8 | 12/2015 |
| WO | WO 2016/135582 A1 | 9/2016 |
| WO | WO 2017/032840 A1 | 3/2017 |
| WO | WO 2017/153186 A1 | 9/2017 |
| WO | WO 2018/154104 A1 | 3/2018 |
| WO | WO 2018/065365 A1 | 4/2018 |
| WO | 2019/110734 A1 | 6/2019 |

OTHER PUBLICATIONS

Wilting, Roel H. et al., Drug Resistance Updates, "Epigenetic mechanisms in tumorigenesis, tumor cell heterogeneity and drug resistance", 2012, vol. 15, pp. 21-38 (Year: 2012).*
International Search Report relating to International Patent Application No. PCT/EP2018/054644, filed on Feb. 26, 2018. International Search Report dated May 3, 2018.
Written Opinion of the International Search Authority relating to International Patent Application No. PCT/EP2018/054644, filed on Feb. 26, 2018. Written Opinion dated May 3, 2018.
International Search Report relating to International Patent Application No. PCT/EP2017/054324, filed on Feb. 24, 2017. International Search Report dated May 2, 2017.
Written Opinion of the International Search Authority relating to International Patent Application No. PCT/EP2017/054324, filed on Feb. 24, 2017. Written Opinion dated May 2, 2017.
International Search Report relating to International Patent Application No. PCT/EP2016/070097, filed on Aug. 25, 2016. International Search Report dated Oct. 12, 2016.
Written Opinion of the International Search Authority relating to International Patent Application No. PCT/EP2016/070097, filed on Aug. 25, 2016. Written Opinion dated Oct. 12, 2016.
International Search Report relating to International Patent Application No. PCT/EP2017/074983, filed on Oct. 2, 2017. International Search Report dated Nov. 16, 2017.
Written Opinion of the International Search Authority relating to International Patent Application No. PCT/EP2017/074983, filed on Oct. 2, 2017. Written Opinion dated Nov. 16, 2017.

Alinari et al., "Selective inhibition of progen argrinine methyltransferase 5 blocks initiation and maintenance of B-cell transformation.", Blood, Apr. 16, 2015, pp. 2530-2543, vol. 125(16).
Andreu-Pérez, P. et al., "Protein Arginine Methyltransferase 5 Regulates ERK ½ Signal Transduction Amplitude and Cell Fate Through CRAF", Sci. Signal, (2011), p. ra58, vol. 4, No. 190.
Antonysamy, S., et al., "Crystal structure of the human PRMT5:MEP50 complex", Proc. Natl Acad Sci, (2012), pp. 17960-17965, vol. 109, No. 44.
Barbash, O., et al., "Abstract LB-248: Protein arginine methyltransferase 5 (PRMT5) inhibition as a therapeutic strategy in B-cell lymphoma", Cancer Research, (2015), see Abstract.
Bezzi, M., et al., "Regulation of constitutive and alternative splicing by PRMT5 reveals a role for Mdm4 pre-mRNA in sensing defects in the spliceosomal machinery", Genes & Development, (2013), pp. 1903-1916, vol. 27, No. 17.
Braun, C.J., et al., "Coordinated Splicing of Regulatory Detained Introns within Oncogenic Transcripts Creates an Exploitable Vulnerability in Malignant Glioma", Cancer Cell, (2017), pp. 411-426, vol. 32, No. 4.
Bundegaard, H., "Design of Prodrugs", Elsevier, New York-Oxford, (1985), pp. 1-92.
Chan-Penebre, E., et al., "A selective inhibitor of PRMT5 with in vivo and in vitro potency in MCL models", Nature Chemical Biology, (2015), pp. 432-437, vol. 11, No. 6.
Cheson et al., "Clinical application and proposal for modification of the International Working Group (IWG) response criteria in myelodysplasia.", Blood, 2006, pp. 419-425, vol. 108(2).
Crane et al., "Synthesis of Pyrrolo[3,2-d]pyrimidines from Furazano[3,4-d]pyrimidines via Enolate and Ene Adducts$^{1a,b}$", Journal of Organic Chemistry, 1980, pp. 3827-3831, vol. 45(19).
Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.
Devkota, K., et al., "Analogues of the Natural Product Sinefungin as Inhibitors of EHMT1 and EHMT2", ACS Med Chem Lett, (2014), pp. 293-297, vol. 5.
Di Lorenzo, A., et al., "Histone arginine methylation", FEBS Letters, (2011), pp. 2024-2031, vol. 585, No. 13.
Eisenhauer et al., "New response evaluation criteria in solid tumours: Revised RECIST guideline (version 1.1).", European Journal of Cancer, 2009, pp. 228-247, vol. 45.
Friesen, W.J., et al., "The Methylosome, a 20S Complex Containing JBP1 and pICIn, Produces Dimethylarginine-Modifiied Sm Proteins", Molecular and Cellular Biology, (2001), pp. 8289-8300, vol. 21, No. 24.
Geoghegan, V., et al., "Comprehensive identification of arginine methylation in primary T cells reveals regulatory roles in cell signaling", Nature Communications, (2015), p. 6758, vol. 6.
Gu, Z., et al., "Protein arginine methyltransferase 5 is essential for growth of lung cancer cells", Biochem J., (2012), pp. 235-241, vol. 446, No. 2.
Hsu, J.M., et al., "Crosstalk between Arg 1175 methylation and Tyr 1173 phosphorylation negatively modulates EGFR-mediated ERK activation", Nature Cell Biology, (2011), pp. 174-181, vol. 13, No. 2.
Hu, H., et al., "Small Molecule Inhibitors of Protein Arginine Methyltransferase", Expert Opinion on Investigational Drugs, (2016), pp. 335-358, vol. 25, No. 3.
Jansson, M., et al., "Arginine methylation regulates the p53 response", Nature Cell Biology, (2008), pp. 1431-1439, vol. 10, No. 12.
Karkhanis, V., et al., "Versatility of PRMT5-induced methylation in growth control and development", Trends in Biochemical Sciences, (2011), pp. 633-641, vol. 36, No. 12.
Kung, P.P., et al., "Design, synthesis, and biological evaluation of novel human 5'-deoxy-5'-methylthioadenosine phosphorylase (MTAP) substrates", Bioorganic & Medicinal Chemistry Letters, (2005), pp. 2829-2833, vol. 15.
March, J., "Advanced Organic Chemistry—Reactions, Mechanisms, and Structure", John Wiley & Sons, Inc., (2002), 4th Edition, A Wiley-Interscience Publication, see Table of Contents.
Matsubara, S., et al., "[2+1] Cycloaddition reaction of bis(iodozincio)methane with 1,2-diketones: face-to-face complex of

(56) References Cited

OTHER PUBLICATIONS bis(iodozincio)methane and 1,2-diketones as a reaction intermediate", Tetrahedron, (2002), pp. 8255-8262, vol. 58.
Moukha-Chafiq, O., et al., "Synthesis and General Biological Activity of a Small Adenosine-5'-(Carboxamide and Sulfanilamide) Library", Nucleosides, Nucleotides and Nucleic Acids, (2014), pp. 709-729, vol. 33, No. 11.
Pal, S., et al., "Low levels of miR-92b/96 induce PRMT5 translation and H3R3 methylation in mantle cell lymphoma", The EMBO Journal, (2007), pp. 3558-3569, vol. 26, No. 15.
Penebre, E., et al., "Identification of a First-in-Class PRMT5 Inhibitor with Potent in Vitro and in Vivo Activity in Preclinical Models of Mantle Cell Lymphoma", Blood, (2014), pp. 438, vol. 124(21), see Abstract.
Prasad, R.N., et al., "Modification of the 5' Position of Purine Nucleosides. 2. Synthesis and Some Cardiovascular Properties of Adenosine-5'-(N-substituted)carboxamides1,2", J. Med. Chem., (1980), pp. 313-319, vol. 23, No. 3.
Schmidt, R.R., et al., "Synthese 5'-modifizierter Adenosinderivate", Chemische Berichte, (1968), pp. 590-594, vol. 101, No. 2.
Shendure, J., et al., "Next-generation DNA sequencing", Nature Biotechnolgoy, (2008), pp. 1135-1145, vol. 26, No. 10.
Shilo, K., et al., "Cellular localization of protein arginine methyltransferase-5 correlates with grade of lung tumors", Diagnostic Pathology, (2013), pp. 1-9, vol. 8, No. 201.
Stahl, P.H., et al., "Handbook of Pharmaceutical Salts: Properties, Selection, and Use", Journal of Medicinal Chemistry, Book Reviews, (2003), pp. 1277-1278, vol. 46, No. 7.
Stopa, N., et al., "The PRMT5 arginine methyltransferase: many roles in development, cancer and beyond", Cell. Mol. Life Sci., (2015), pp. 2041-2059, vol. 72, No. 11.
Vuilhorgne, M., et al., "New Synthetic S-Adenosyl-Homocysteine Analogues with Oncostatic and Antiviral Activity", HETEROCYLCES, 1978, pp. 495-520, vol. 11, XP009112700.
Wang, L., et al., "Protein Arginine Methyltransrerase 5 Suppresses the Transcription of the RB Family of Tumor Suppressors in Leukemia and Lymphoma Cells", Molecular and Cellular Biology, (2008), pp. 6262-6277, vol. 28, No. 20.
Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.
Wei, H., et al., "PRMT5 dimethylates R30 of the p65 subunit to activate NF-κB", Proc Natl Acad Sci USA, (2013), pp. 13516-13521, vol. 110, No. 33.
Wei, T.Y.W., et al., "Methylosome protein 50 promotes androgen- and estrogen-independent tumorigenesis", Cellular Signaling, (2014), pp. 2940-2950, vol. 26.
Zhao, Q., et al., "PRMT5-mediated methylation of histone H4R3 recruits DNMT3A, coupling histone and DNA methylation in gene silencing", Nat Struct Mol Biol, (2009), pp. 304-311, vol. 16, No. 3.
Gerhart et al., "Activation of the p53-MDM4 regulatory axis defines the anti-tumour response to PRMT5 inhibition through its role in regulating cellular splicing.", Scientific Reports, Jun. 26, 2018, pp. 1-15, vol. 8(1), XP055625791.
Wu et al., "Abstract 4859: JNJ-64619178, a selective and pseudo-irreversible PRMT5 inhibitor with potent invitro and invivo activity, demonstrated in several lung cancer models.", Experimental and Molecular Therapeutics, Jul. 2018, XP055668420, Retrieved from the Internet: URL:https://www.semanticschol ar.org/paper/Abstract-4859:-JNJ-64619178,-a-selective-and-PRMT5-Wu-Millar/a6583b4db0edbaefacf2 888b121 f87e020d6889e.
Millar et al., "Abstract 950: In vivo efficacy and pharmacodynamic modulation of JNJ-64619178, a selective PRMT5 inhibitor, in human lung and hematologic preclinical models.", Cancer Research, AACR Annual Meeting 2019; Mar. 29-Apr. 3, 2019, XP055668372.
Guo et al., "Abstract 3905:Translational efficacy and safety modeling and simulation to support the clinical development of JNJ-64619178, a PRMT5 inhibitor.", Cancer Research, AACR Annual Meeting 2019; Mar. 29-Apr. 3, 2019, XP055668379.
Lin et al., "Nucleoside protein arginine methyl transferase 5 (PRMT5) inhibitors.", Bioorganic & Medicinal Chemistry Letters, Jun. 1, 2019, pp. 1264-1269, vol. 29(11), XP055663652.
International Search Report and Written Opinion relating to International Patent Application No. PCT/EP2020/065639, filed Jun. 5, 2020. International Search Report and Written Opinion dated Aug. 26, 2020.
Boyer et al., "Adenosine kinase inhibitors. 5. Synthesis, enzyme inhibition, and analgesic activity of diaryl-erythro-furanosyltubercidin analogues," J Med Chem, vol. 48, Issue 20, 2005, pp. 6430-6441.
Brand et al., "Synthesis of [n,5]-Spiroketals by Ring Enlargement of Donor Acceptor-Substituted Cyclopropane Derivatives", JOC, vol. 74, 2009, pp. 8779-8786.
Colombian office action dated Sep. 12, 2019, relating to co-pending Colombian patent application No. NC2018/0002063.
Dermer, "Another Anniversary for the War on Cancer", Biotechnology, vol. 12, 1994, p. 320.
European Search Report; EP Patent Application No. EP Patent Application No. 15184011.3; Report dated Oct. 22, 2015.
Evans, et al., "Pharmacogenomics: Translating Functional Genomics into Rational Therapeutics", Science, vol. 286, 1999, pp. 487-491.
Graubert, et al., "Recurrent mutations in the U2AF 1 splicing factor in myelodysplastic syndromes", Nature Genetics, vol. 44, Jan. 2012, pp. 53-59.
Guo et al., "STING Agonists Induce an Innate Antiviral Immune Response against Hepatitis B Virus", Antimicrobial Agents and Chemotherapy vol. 59, No. 2, Feb. 1, 2015, pp. 1273-1281.
Herrera et al., "Stereocontrolled photocyclization of 1,2-diketones: application of a 1,3-acetyl group transfer methodology to carbohydrates," Journal of Organic Chemistry, vol. 73, Mar. 2008, pp. 3384-3391.
HUGO Gene Nomenclature Committee (HGNC) reports for the Major Spliceosome found online at https://www.genenames.org/data/genegroup/#!/group/1518 and accessed Apr. 20, 2021.
International Report on Patentability; International Patent Application No. PCT/EP2016/070097; Report dated Feb. 27, 2018.
Li, et al., A patent review of arginine methyltransferase inhibitors, Expert Opinion on Therapeutic Patents, vol. 29, No. 2, 2019, pp. 97-114.
Nowak et al., "Addition of Difluorocarbene to 4',5'-Unsaturated Nucleosides: Synthesis and Deoxygenation Reactions of Difluorospirocyclopropane Nucleosides1", JOC, vol. 71, 2006, pp. 8876-8883.
Ramakrishma et al., "Stereoselective synthesis of 1,6-dioxaspirolactones from spiro-cyclopropanecarboxylated sugars: total synthesis of dihydro-pyrenolide D†", RSC Adv., vol. 5, 2015, pp. 8142-8145.
Redlich et al., "Chiral Cyclobutanones by [2 + 2]-Cycloaddition of Dichloroketene to Carbohydrate En01 Ethers", Angewe Chem., Int. Ed. Engl., vol. 28, 1989, pp. 777-778.
Tiwari et al., "Synthesis and Anticancer Evaluation of 4'-C-Methyl-2'-Fluoro Arabino Nucleosides", Nucleotides and Nucleic Acids, vol. 28, Nos. 5-7, 2009, pp. 657-677.
Werz et al., "Synthesis of [n,5]-Spiroketals by Ring Enlargement of Donor-Acceptor-Substituted Cyclopropane Derivatives", J Org. Chem., vol. 74, 2009, pp. 8779-8786.
Wuts, P.G.M. and Greene, Protective Groups in Organic Synthesis, Fourth Edition, Wiley, New York, 2006.
Xiong, et al., Driver Genes as Targets for Lung Cancer Prevention and Treatment Progress in Chemistry, Sep. 9, 2013, vol. 25, pp. 1517-1525.
Fitchen, J.H, et al. "Methylthioadenosine phosphorylase deficiency in human leukemias and solid tumors," Cancer research. vol. 46, No. 10, Oct. 1986, pp. 5409-5412.
Nobori T, et al. "Methylthioadenosine phosphorylase deficiency in human non-small cell lung cancers". Cancer research. Vol. 53, No. 5, Mar. 1, 1993, pp. 1098-1101.

(56) References Cited

OTHER PUBLICATIONS

Nobori, T, et al. "Genomic cloning of methylthioadenosine phosphorylase: a purine metabolic enzyme deficient in multiple different cancers". Proceedings of the National Academy of Sciences, vol. 93, No. 12, Jun. 11, 1996, pp. 6203-6208.

\* cited by examiner

Note: Line under X-axis represents the dosing period.

METHODS OF TREATING CANCER USING PRMT5 INHIBITORS

CROSS-REFERENCE TO RELATED APPLICATIONS

This application claims the benefit of the priority of U.S. Provisional Patent Application No. 62/858,076, filed Jun. 6, 2019, and European Patent Application No. 19193850.5, filed Aug. 27, 2019, the disclosures of which are incorporated by reference herein in their entireties.

FIELD OF THE INVENTION

The present invention relates to methods of treating cancers using PRMT5 inhibitors.

BACKGROUND

Protein Arginine Methyltransferase 5 (PRMT5), also described as Hs17, Jbp1, Skb1, Capsuleen or Dart5, is one of the major methyltransferases responsible for mono- and symmetric dimethylation of arginines. Post-translational arginine methylation on histones and non-histone proteins seems to be crucial for a variety of biological processes, like genome organisation, transcription, differentiation, spliceosome function, signal transduction and regulation of cell-cycle progression, stem cells and T-cell fate. Metazoan PRMT5 forms a functional complex with the methylosome protein 50 (MEP50) also named as Wdr77, androgen receptor coactivator p44 and Valois. Both elevated PRMT5-MEP50 protein level and cytoplasmic accumulation are implicated in cancer tumorigenesis and have been correlated with poor clinical outcome. Cellular rescue experiments that addressed both the catalytic and scaffold function of the PRMT5-MEP50 complex and beside comprehensive enzymological studies have substantiated the oncogenic link between protein level, localisation and enzymatic function. This correlation turns PRMT5 into an important small molecule drug target against cancer and other diseases.

Although PRMT5 is considered a clinically relevant target, very few selective PRMT5 inhibitors have been developed. There is thus a strong need for novel treatment regimens involving PRMT5 inhibitors for the treatment or prevention of cancer. It is accordingly an object of the present disclosure to provide such methods.

SUMMARY

JNJ-64619178 is a potent and selective small molecule inhibitor across a broad array of heme and solid tumor cell lines, with potential differentiating characteristics in that it binds simultaneously to the cofactor SAM and the substrate pockets of the (PRMT5)4/(MEP50)4 complex (methylosome) with a long-residence time, particularly compared to other PRMT5 inhibitors. In vivo data demonstrate regressions/cures in all human xenograft models tested at tolerable doses, with no ADME or developability issues and with PK and toxicity profiles suitable for ≤QD oral dosing in humans.

In certain embodiments, the disclosure provides methods for treating a human patient diagnosed with a cancer, comprising administering a therapeutically effective amount of a PRMT5 (protein arginine methyltransferase 5) inhibitor, the method comprising (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and (ii) administering to the patient subsequent doses of at least about 0.1 mg per day of the PRMT5 inhibitor for one or more subsequent dosing periods of about 5 to about 20 days each. In these methods, a first subsequent dosing period is separated in time from the initial dosing period by at least about 5 days and/or the subsequent dosing periods are separated in time from each other by at least about 5 days.

In further embodiments, the disclosure provides methods for treating a human patient diagnosed with a cancer, comprising administering a therapeutically effective amount of a PRMT5 (protein arginine methyltransferase 5) inhibitor, the method comprising (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 21 days; and (ii) administering to the patient subsequent doses of at least about 0.1 mg per day of the PRMT5 inhibitor for one or more subsequent dosing periods of about 5 to about 21 days each. In these methods, a first subsequent dosing period is separated in time from the initial dosing period by at least about 5 days and/or the subsequent dosing periods are separated in time from each other by at least about 5 days.

In other embodiments, the disclosure provides methods for treating a human patient diagnosed with a cancer, comprising administering a therapeutically effective amount of a PRMT5 inhibitor, the method comprising (i) administering to the patient initial doses of at least about 0.1 mg per day of the PRMT5 inhibitor that is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days; and (ii) administering to the patient subsequent doses of at least about 0.1 mg per day of the PRMT5 inhibitor for one or more subsequent dosing periods. In these methods, a first subsequent dosing period is separated in time from the initial dosing period by at least about 7 days and/or the subsequent dosing periods are separated in time from each other by at least about 7 days.

In further embodiments, the disclosure provides methods for treating a human patient diagnosed with a cancer, comprising administering a therapeutically effective amount of a PRMT5 inhibitor, the method comprising (i) administering to the patient initial doses of at least about 0.1 mg per day of the PRMT5 inhibitor that is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days; (ii) after the initial period, administering to the patient no doses of the PRMT5 inhibitor for an off-period of about 7 days; (iii) after the off-period, administering to the patient subsequent doses of at least about 0.1 mg per day of the PRMT5 inhibitor for a subsequent dosing period of about 14 days; (iv) after the subsequent dosing period, administering to the patient no doses of the compound for an off-period of about 7 days; and (v) optionally, sequentially repeating steps (iii) and (iv).

In other embodiments, the disclosure provides methods for treating a human patient diagnosed with a cancer, comprising administering a therapeutically effective amount of a PRMT5 inhibitor, the method comprising (i) administering to the patient initial doses of at least about 0.1 mg per day of the PRMT5 inhibitor that is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days; (ii) after the initial period, administering to the patient no doses of the PRMT5 inhibitor for an off-period of about 14 days; (iii) after the off-period, administering to the patient subsequent doses of at least about 0.1 mg per day of the PRMT5 inhibitor for a subsequent dosing period of about 14 days; (iv) after the subsequent dosing period, administering to the patient no doses of the compound for an off-period of about 14 days; and (v) optionally, sequentially repeating steps (iii) and (iv).

In yet other embodiments, the disclosure provides methods for treating a human patient diagnosed with a cancer, comprising administering a therapeutically effective amount of a PRMT5 inhibitor, the method comprising (i) administering to the patient initial doses of at least about 0.1 mg per day of the PRMT5 inhibitor that is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 7 days; (ii) after the initial period, administering to the patient no doses of the PRMT5 inhibitor for an off-period of about 7 days; (iii) after the off-period, administering to the patient subsequent doses of at least about 0.1 mg per day of the PRMT5 inhibitor for a subsequent dosing period of about 7 days; (iv) after the subsequent dosing period, administering to the patient no doses of the compound for an off-period of about 7 days; and (v) optionally, sequentially repeating steps (iii) and (iv).

In still further embodiments, the disclosure provides PRMT5 (protein arginine methyltransferase 5) inhibitors for use in treating a human patient diagnosed with a cancer by administration of a therapeutically effective amount of the PRMT5 inhibitor to the human patient, wherein the administration comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days.

In further embodiments, the disclosure provides PRMT5 (protein arginine methyltransferase 5) inhibitors for use in treating a human patient diagnosed with a cancer by administration of a therapeutically effective amount of the PRMT5 inhibitor to the human patient, wherein the administration comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 21 days; and (ii) administering to the patient subsequent doses of at least about 0.1 mg per day of the PRMT5 inhibitor for one or more subsequent dosing periods of about 5 to about 21 days each; wherein, a first subsequent dosing period is separated in time from the initial dosing period by at least about 5 days; and the subsequent dosing periods are separated in time from each other by at least about 5 days.

In other embodiments, the disclosure provides PRMT5 (protein arginine methyltransferase 5) inhibitors for use in methods of treating a human patient diagnosed with a cancer, wherein the method comprises administering a therapeutically effective amount of the PRMT5 inhibitor to the human patient, wherein the method comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days.

In yet further embodiments, the disclosure provides PRMT5 (protein arginine methyltransferase 5) inhibitors for use in methods of treating a human patient diagnosed with a cancer, wherein the method comprises administering a therapeutically effective amount of the PRMT5 inhibitor to the human patient, wherein the method comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 21 days; and (ii) administering to the patient subsequent doses of at least about 0.1 mg per day of the PRMT5 inhibitor for one or more subsequent dosing periods of about 5 to about 21 days each; wherein, a first subsequent dosing period is separated in time from the initial dosing period by at least about 5 days; and the subsequent dosing periods are separated in time from each other by at least about 5 days.

In other embodiments, the disclosure provides methods for treating a human patient diagnosed with a cancer, comprising administering a therapeutically effective amount of a PRMT5 (protein arginine methyltransferase 5) inhibitor, the method comprising administering to the patient a continuous dose of about up to about 2 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for a dosing period of at least about 21 days. In some aspects, the continuous dose is about 1 mg to about 2 mg per day of the PRMT5 inhibitor. In other aspects, the continuous dose is about 1 mg per day of the PRMT5 inhibitor. In further aspects, the continuous dose is about 2 mg per day of the PRMT5 inhibitor.

In further embodiments, the disclosure provides PRMT5 (protein arginine methyltransferase 5) inhibitors for use in methods of treating a human patient diagnosed with a cancer, wherein the method comprises administering a therapeutically effective amount of the PRMT5 inhibitor to the human patient, wherein the method comprises administering to the patient a continuous dose of up to about 2 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for a dosing period of at least about 21 days. In some aspects, the continuous dose is about 1 mg to about 2 mg per day of the PRMT5 inhibitor. In other aspects, the continuous dose is about 1 mg per day of the PRMT5 inhibitor. In further aspects, the continuous dose is about 2 mg per day of the PRMT5 inhibitor.

In still further embodiments, the disclosure provides a PRMT5 (protein arginine methyltransferase 5) inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for use in treating a human patient diagnosed with a cancer by administration of a therapeutically effective amount of the PRMT5 inhibitor to the human patient, wherein the administration comprises: (i) administering to the patient initial doses of at least about 0.1 mg per day of the PRMT5 inhibitor for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days.

In further embodiments, the disclosure provides a PRMT5 (protein arginine methyltransferase 5) inhibitor that is that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for use in treating a human patient diagnosed with a cancer by administration of a therapeutically effective amount of the PRMT5 inhibitor to the human patient, wherein the administration comprises: (i) administering to the patient initial doses of at least about 0.1 mg per day of the PRMT5 inhibitor for an initial dosing period of about 5 to about 21 days; and (ii) administering to the patient subsequent doses of at least about 0.1 mg per day of the PRMT5 inhibitor for one or more subsequent dosing periods of about 5 to about 21 days each; wherein, a first subsequent dosing period is separated in time from the initial dosing period by at least about 5 days; and the subsequent dosing periods are separated in time from each other by at least about 5 days.

In other embodiments, the disclosure provides a PRMT5 (protein arginine methyltransferase 5) inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for use in methods of treating a human patient diagnosed with a cancer, wherein the method comprises administering a therapeutically effective amount of the PRMT5 inhibitor to the human patient, wherein the method comprises: (i) administering to the patient initial doses of at least about 0.1 mg per day of the PRMT5 inhibitor for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days.

In yet further embodiments, the disclosure provides a PRMT5 (protein arginine methyltransferase 5) inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for use in methods of treating a human patient diagnosed with a cancer, wherein the method comprises administering a therapeutically effective amount of the PRMT5 inhibitor to the human patient, wherein the method comprises: (i) administering to the patient initial doses of at least about 0.1 mg per day of the PRMT5 inhibitor for an initial dosing period of about 5 to about 21 days; and (ii) administering to the patient subsequent doses of at least about 0.1 mg per day of the PRMT5 inhibitor for one or more subsequent dosing periods of about 5 to about 21 days each; wherein, a first subsequent dosing period is separated in time from the initial dosing period by at least about 5 days; and the subsequent dosing periods are separated in time from each other by at least about 5 days.

In further embodiments, the disclosure provides a PRMT5 (protein arginine methyltransferase 5) inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for use in methods of treating a human patient diagnosed with a cancer, wherein the method comprises administering a therapeutically effective amount of the PRMT5 inhibitor to the human patient, wherein the method comprises administering to the patient a continuous dose of up to about 2 mg per day of the PRMT5 inhibitor for a dosing period of at least about 21 days. In some aspects, the continuous dose is about 1 mg to about 2 mg per day of the PRMT5 inhibitor. In other aspects, the continuous dose is about 1 mg per day of the PRMT5 inhibitor. In further aspects, the continuous dose is about 2 mg per day of the PRMT5 inhibitor. In the following passages, different aspects and embodiments of the disclosure are defined in more detail. Each aspect or embodiment so defined may be combined with any other embodiment, embodiments, aspect or aspects unless clearly indicated to the contrary. In particular, any feature indicated as being preferred or advantageous may be combined with any other feature or features indicated as being preferred or advantageous.

DETAILED DESCRIPTION

Figure 1:
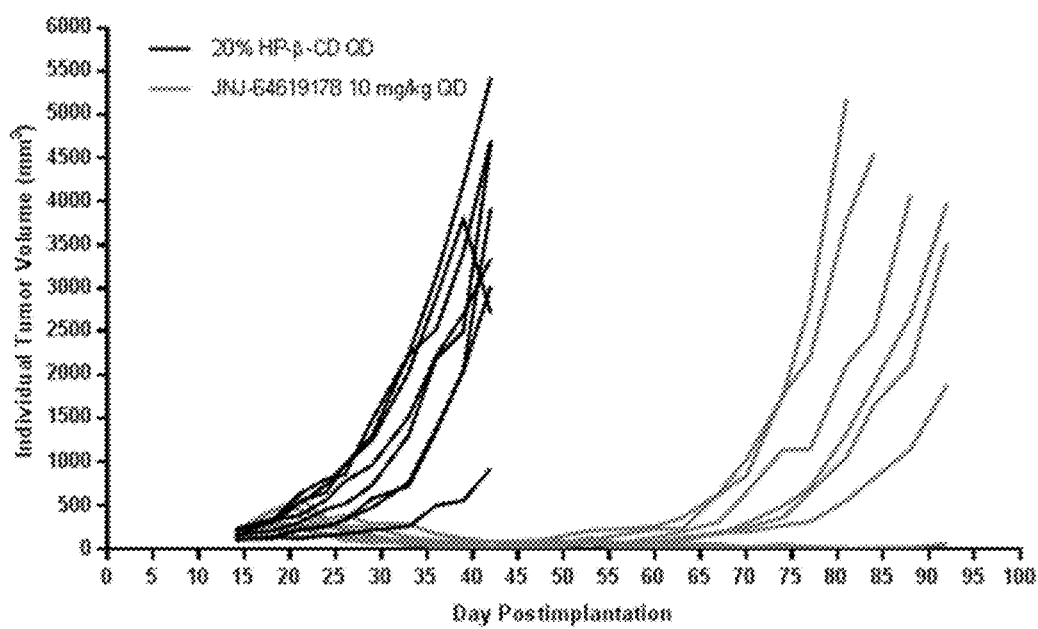
FIG. 1 is a line graph showing extended tumor growth inhibition using a dosing cessation of the compound of the disclosure in the NCI-H1048 tumor model (tumor regrowth observed following dosing cessation of JNJ-64619178 in human SCLC mouse xenograft).

JNJ-64619178 is a S-adenosylmethionine (SAM) competitive small molecule inhibitor of PRMT5/MEP50 which exhibits slow off-rate binding kinetics as demonstrated by surface plasmon resonance binding studies. Additional in vitro thermal shift experiments show that binding of JNJ-64619178 stabilizes the PRMT5/MEP50 complex by an additional 12 degrees Celsius in comparison to SAM binding. Co-crystallization of JNJ-64619178 with PRMT5/MEP50 indicates that binding is in the SAM binding pocket. Additional binding of JNJ-64619178 into the protein substrate binding pocket appears to trap the whole PRMT5/MEP50 protein complex in an inactive state, which explains the molecular mechanism of the slow off-rate binding kinetics. This unique mode-of-binding translates into very potent and time-dependent PRMT5 enzyme inhibition.

As described herein, the methods are directed to treating human patients diagnosed with a cancer by using (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol (a PRMT5 inhibitor also referred to as JNJ-64619178) and a novel dosing schedule. According to particular embodiments, a dosing schedule comprising "on/off dosing cycles" not only results in equivalent or superior efficacy of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol (e.g., compared to a continuous dosing cycle in which there are no "off periods"), but may provide prolonged pharmacodynamic modulation during periods where no (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol is administered to the patient. Thus, according to certain embodiments, tumor growth continues to be suppressed and the plasma drug concentration is maintained during washout periods or "off periods". Preferably, dosing schedules that include "off periods" may have a lower risk of toxicities compared to continuous dosing schedules with no "off periods." Dosing schedules that include "off periods" may also, or alternatively, result in increased recovery from toxicities compared to recovery from toxicities that is seen when continuous dosing schedules with no "off periods" are utilized. According to particular embodiments, a patient that is administered the JNJ-64619178 PRMT5 inhibitor according to a dosing schedule comprising "on/off dosing cycles" over a period of time (e.g., 3 months, 6 months, 9 months, 12 months, 18 months, or 24 months) may experience fewer toxicities compared to a patient that is administered the same dose of JNJ-64619178 PRMT5 inhibitor over the same period of time but according to a "continuous" dosing schedule that does not include any "off periods." According to other embodiments, a patient that is administered the JNJ-64619178 PRMT5 inhibitor according to a dosing schedule comprising "on/off dosing cycles" over a period of time (e.g., 3 months, 6 months, 9 months, 12 months, 18 months, or 24 months) may experience fewer dose interruptions compared to a patient that is administered the same dose of JNJ-64619178 PRMT5 inhibitor over the same period of time but according to a "continuous" dosing schedule that does not include any "off periods."

As described herein, the disclosure also provides methods for treating a human patient diagnosed with a cancer via a continuous dosing regimen. Such methods lack "off periods", thereby providing a consistent daily pharmacokinetic profile. Such methods comprise administering a continuous dose of the PRMT5 inhibitor that is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof to the patient. In some embodiments, the dosing period is at least about 21 days. In some aspects, the continuous dose is about 1 mg to about 2 mg per day of the PRMT5 inhibitor. In other aspects, the continuous dose is about 1 mg per day of the PRMT5 inhibitor. In further aspects, the continuous dose is about 2 mg per day of the PRMT5 inhibitor.

Methods of the present disclosure comprise administering a therapeutically effective amount of a PRMT5 inhibitor. The term "therapeutically effective amount" refers to an amount (e.g., of an active compound or pharmaceutical agent, such as a compound of the present disclosure), which elicits the biological or medicinal response in a tissue system, animal or human that is being sought by a researcher, veterinarian, medical doctor or other clinician, including reduction or inhibition of an enzyme or a protein activity, or ameliorating symptoms, alleviating conditions, slowing or delaying disease progression, or preventing a disease. Stated another way, the term therapeutically effective amount may refer to an amount that, when administered to a particular subject, achieves a therapeutic effect by inhibiting, alleviating or curing a disease, condition, syndrome or disorder in the subject or by prophylactically inhibiting, preventing or delaying the onset of a disease, condition, syndrome or disorder, or symptom(s) thereof. A therapeutically effective amount may be an amount which relieves to some extent one or more symptoms of a disease, condition, syndrome or disorder in a subject; and/or returns to normal either partially or completely one or more physiological or biochemical parameters associated with or causative of the disease, condition, syndrome or disorder; and/or reduces the likelihood of the onset of the disease, condition, syndrome or disorder, or symptom(s) thereof.

The term "PRMT5 inhibitor" or "protein arginine methyltransferase 5 inhibitor" as used herein refers to a chemical compound that inhibits enzymatic activity of protein arginine methyltransferase 5. In some embodiments, the PRMT5 inhibitor is a compound discussed herein. In other embodiments, the PRMT5 inhibitor is (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof. In further embodiments, the PRMT5 inhibitor is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol. In yet other embodiments, the PRMT5 inhibitor is a salt of (1 S,2R,3 S,5R)-3-(2-(2-amino-3-bromoquinolin-7-yl)ethyl)-5-(4-amino-7H-pyrrolo[2,3-d]pyrimidin-7-yl)cyclopentane-1,2-diol. In still further embodiments, the PRMT5 inhibitor is a solvate of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol. Unless noted to the contrary herein, one skilled in the art would understand that the PRMT5 inhibitor used in the subsequent doses is the same as the PRMT5 inhibitor used for the initial doses.

According to particular embodiments, efficacy of the methods described herein is measured by techniques, such as determining a patient time to disease progression or a patient response rate. As such, efficacy may be useful in determining whether treatment may be continued or discontinued. In some embodiments, efficacy is measured by determining the patient's time to disease progression, e.g., a reduction in disease progression over time in response to treatment according to a method of the present disclosure. The disease progression may be measured by proliferation of the cancer cells (locally or systemically), and/or reoccurrence of side effects of the disease, and/or occurrence of new side effects of the disease. Thus, in some embodiments, the methods described herein desirably increase the time to disease progression of the patient, relative to the disease progression of the patient prior to method initiation.

In other embodiments, the efficacy is measured by determining a patient response rate. The "response rate" as used herein is the ratio of the number patients who respond to treatment (by a demonstration of efficacy) to the number of patients who have been treated. One of skill in the art would readily be able to assess a patient's response rate using standardized classifications and criteria including, without limitation, the Lugano staging classification (See, Table 1) and Response Evaluation Criteria in Solid Tumors (RECIST), among others. See, e.g., Eisenhauer et al., New response evaluation criteria in solid tumours: Revised RECIST guideline (version 1.1), European Journal of Cancer, 45:228-247 (2009), which is incorporated by reference herein. As stated therein, Complete Response (CR) includes disappearance of all target lesions; Partial Response (PR) includes at least a 30% decrease in the sum of diameters of target lesions, taking as reference the baseline sum diameters; Progressive Disease (PD) includes at least a 20% increase in the sum of diameters of target lesions, taking as reference the smallest sum on study (this includes the baseline sum if that is the smallest on study); and Stable Disease (SD) includes neither sufficient shrinkage to qualify for PR nor sufficient increase to qualify for PD, taking as reference the smallest sum diameters while on study.

about 30%, at least about 35%, at least about 40%, at least about 45%, or at least about 50% following treatment. In other embodiments, the methods are effective in reducing a tumor volume by at least about 30% or about 35%.

In other aspects, the methods are effective in treating hematological cancers by, e.g., stabilizing one or more hematological parameter. Examples of hematological parameters that may be measured to evaluate efficacy include, without limitation, a complete blood count, e.g., red blood cells (RBC), white blood cells (neutrophils, eosinophils, basophils, monocytes and lymphocytes), platelets, haemoglobin, haematocrit, or combinations thereof. The effectiveness of the claimed methods in treating hematological cancers may be measured by RBC transfusion independence (TI) rate, overall improvement rate (complete remission, partial remission, and hematologic improvement), or a combination thereof. In some embodiments, the response criteria for patients with MDS are determined using the modified International Working Group response criteria. See, e.g., Cheson B D, Greenberg P L, Bennett J M, et al. Clinical application and proposal for modification of the International Working Group (IWG) response criteria in myelodysplasia, Blood, 108:419-425, 2006, which is incorporated herein by reference.

In other embodiments, the methods permit the patient to maintain a stable condition or state, i.e., where the cancer does not progress or otherwise adversely impact the patient.

According to additional embodiments, the method of treatment is effective in causing the patient to go into remission from cancer.

As detailed herein, the methods comprise administering to the patient initial doses of the PRMT5 inhibitor for an initial dosing period, e.g., on a daily basis. In some embodiments,

TABLE 1

| Lugano Staging Classification | |
|---|---|
| Limited | |
| Stage I | one node or group of adjacent nodes |
| Stage II | two or more nodal groups, same side |
| Advanced | |
| Stage III | nodes on both sides of the diaphragm; nodes above the diaphragm with spleen involvement |
| Stage III(1) | involvement of the spleen or splenic, hilar, celiac, or portal nodes |
| Stage III(2) | involvement of the para-aortic, iliac, inguinal, or mesenteric nodes |
| Stage IV | diffuse or disseminated involvement of one or more extranodal organs or tissue beyond that designated E, with or without associated lymph node involvement |

According to particular embodiments, methods of the present invention are effective in bringing about a complete response (CR), or partial response (PR), or stable disease (SD) in a patient, in accordance with the RECIST criteria.

According to particular embodiments, the efficacy of a treatment method of the present disclosure may be measured by one or more of decrease in proliferation of the cancer cells (locally or systemically), the absence of cancer cells (locally or systemically), decrease of side effects of the disease, or elimination of side effects of the disease. In some embodiments, a method of the present invention is effective in treating solid or hematological cancers.

In some aspects, the methods are effective in treating a solid tumor by, e.g., reducing a tumor volume in the patient. In some embodiments, the tumor volume of the patient decreases by at least about 5%, at least about 10%, at least about 15%, at least about 20%, at least about 25%, at least the patient is already taking the PRMT5 inhibitor on a daily basis. In other embodiments, the patient has not yet been administered the PRMT5 inhibitor. The term "initial dosing period" as used herein refers to the period of time during which administration of the PRMT5 inhibitor or the implementation of the methods described herein is initiated.

According to particular embodiments, the initial dosing period is about 5 to about 20 days or about 5 to about 21 days. In some embodiments, the initial dosing period is about 5, about 6, about 7, about 8, about 9, about 10, about 11, about 12, about 13, about 14, about 15, about 16, about 17, about 18, about 19, about 20 days, or about 21 days. In other embodiments, the initial dosing period is about 7 days to about 14 days. In further embodiments, the initial dosing period is about 7 days. In still other embodiments, the initial dosing period is about 14 days.

The methods also include administering to the patient subsequent doses of the PRMT5 inhibitor for one or more subsequent dosing periods, e.g., on a daily basis. In some embodiments, the PRMT5 inhibitor used in the subsequent doses is the same as the PRMT5 inhibitor used for the initial doses. The term "subsequent dosing period" as used herein refers to a period of time that follows the initial dosing period. The attending physician, or another clinician, may be able to determine the number of subsequent dosing periods that would provide a therapeutic effect or clinical benefit. The attending physician, or another clinician, also may be able to determine when treatment may be discontinued. Desirably, the subsequent dosing periods continue provided that the patient experiences one or more clinical benefits from the treatment. In some embodiments, the subsequent dosing periods continue until the patient is in remission from the disease or condition, e.g., cancer, which prompted administration of the PRMT5 inhibitor; in such cases, administration of the PRMT5 inhibitor may be discontinued. In other embodiments, the subsequent dosing periods continue until the patient exhibits an increase in cancer cells and/or tumor volume. In further embodiments, the subsequent dosing periods continue provided that the treatment is tolerable to the patient. For example, the subsequent dosing periods may continue until the patient exhibits an adverse event where discontinuation of the PRMT5 inhibitor outweighs the severity of the adverse event.

According to particular embodiments, the one or more subsequent dosing period is about 5 to about 20 days each or about 5 to about 21 days each. In some embodiments, the one or more subsequent dosing period is about 5, about 6, about 7, about 8, about 9, about 10, about 11, about 12, about 13, about 14, about 15, about 16, about 17, about 18, about 19, about 20 days, or about 21 days. In other embodiments, the one or more subsequent dosing period is about 7 days to about 14 days. In further embodiments, the one or more subsequent dosing period is about 7 days. In still other embodiments, the one or more subsequent dosing period is about 14 days.

The first subsequent dosing period is separated from the initial dosing period by a period of time. This period of time is also referred to as a "first washout period" or "off-period". During this first washout period, the PRMT5 inhibitor is not administered to the patient. In some embodiments, the first subsequent dosing period is separated from the initial dosing period by at least about 5 days, i.e., the first washout period is at least about 5 days. In other embodiments, the first washout period is about 3, about 4, about 5, about 6, about 7, about 8, about 9, about 10, about 11, about 12, about 13, or about 14 days. In further embodiments, the first washout period is about 7 to about 14 days. In other embodiments, the first washout period is about 7 days. In yet further embodiments, the first washout period is about 14 days.

Each of the subsequent dosing periods are separated from each other by a period of time, i.e., a "washout period" or "off-period". During these subsequent washout periods, the PRMT5 inhibitor is not administered to the patient. In some embodiments, the subsequent dosing periods are separated in time from each other by at least about 5 days. In further embodiments, the subsequent dosing periods are separated in time from each other by at least about 7 days. In other embodiments, the subsequent dosing periods are separated in time from each other by about 3, about 4, about 5, about 6, about 7, about 8, about 9, about 10, about 11, about 12, about 13, or about 14 days. In other embodiments, the subsequent dosing periods are separated in time from each other by at least about 14 days. In yet further embodiments, the subsequent dosing periods are separated in time from each other by 7 days.

In certain embodiments, the first subsequent dosing period is separated in time from the initial dosing period by at least about 7 days and the subsequent dosing periods are separated in time from each other by at least about 7 days. In further embodiments, the first subsequent dosing period is separated in time from the initial dosing period by about 7 days; and the subsequent dosing periods are separated in time from each other by about 7 days. The subsequent dosing periods, subsequent off-periods, or a combination thereof may be sequentially repeated.

Each of the doses, i.e., the initial dose or subsequent doses, may be determined depending on factors such as route of administration, the age and condition of the patient, and the particular disorder or disease being treated. The initial doses and at least one subsequent dose may be the same or may differ. In certain embodiments, the initial dose and at least one subsequent dose are the same. In other embodiments, the initial dose and at least one subsequent dose are different. In certain embodiments, the initial dose and subsequent doses are the same.

The initial doses and each of the subsequent doses may be administered on a daily basis. The doses, both the initial and each subsequent, may be administered as a single dose, i.e., once daily, or divided doses. In some embodiments, the initial doses are administered once daily. In other embodiments, each subsequent dose is administered once daily. In further embodiments, both the initial and at least one subsequent dose are administered once daily. The doses may also be divided doses. The term "divided doses" as used herein refers to the administration of doses at least twice daily. Thus, for example, "divided doses" refers to two times per day (BID), three times per day (TID), or four times per day (QID). In certain embodiments, the initial doses are divided doses. In other embodiments, each of the subsequent doses are divided doses. In further embodiments, the initial dose and at least one subsequent dose are administered in divided doses. Each dose of the divided dose may be the same of may differ. In some embodiments, the divided doses for the initial dose are the same or equal. In other embodiments, the divided doses for the initial dose differ. In further embodiments, the divided doses for each subsequent dose are the same or equal. In still other embodiments, the divided doses for each subsequent dose differ. In further embodiments, the divided doses for the initial and each subsequent dose are equal. In yet other embodiments, the initial dose is administered twice daily. In still further embodiments, the initial dose is administered thrice daily. In other embodiments, the initial dose is administered four times per day. In further embodiments, each subsequent dose is administered twice daily. In still other embodiments, each subsequent dose is administered thrice daily. In yet further embodiments, each subsequent dose is administered four times per day. In other embodiments, each of the initial dose or at least one subsequent dose is administered twice daily in divided doses. In further embodiments, both the initial dose and at least one subsequent dose are administered twice daily in divided doses.

The initial dose per day, i.e., the daily dose, is, independently, at least about 0.1 mg. In some embodiments, the initial dose per day is at least about 0.1 mg. In further embodiments, the initial dose per day is at least about 0.5 mg, at least about 1 mg, at least about 1.5 mg, at least about 2 mg, at least about 3 mg, at least about 4 mg, at least about 5 mg, at least about 5.5 mg, at least about 6 mg, at least about 8 mg, at least about 16 mg, at least about 30 mg, or at least about 60 mg. In yet further embodiments, the initial dose per day is about 0.5 mg. In other embodiments, the initial dose per day is about 1 mg. In other embodiments, the initial dose per day is about 1.5 mg. In further embodiments, the initial dose per day is about 2 mg. In other embodiments, the initial dose per day is about 2.5 mg. In yet other embodiments, the initial dose per day is about 3 mg. In other embodiments, the initial dose per day is about 3.5 mg. In still further embodiments, the initial dose per day is about 4 mg. In other embodiments, the initial dose per day is about 4.5 mg. In other embodiments, the initial dose per day is about 5 mg. In further embodiments, the initial dose per day is about 5.5 mg. In still other embodiments, the initial dose per day is about 6 mg. In yet further embodiments, the initial dose per day is about 8 mg. In other embodiments, the initial dose per day is about 12.5 mg. In further embodiments, the initial dose per day is about 16 mg. In yet other embodiments, the initial dose per day is about 25 mg.

In other embodiments, each of the initial doses, per day, is about 0.1 to about 100 mg. In further embodiments, each of the initial doses, per day, is about 0.5 to about 80 mg. In still other embodiments, each of the initial doses, per day, is about 0.5 to about 60 mg. In yet further embodiments, each of the initial doses, per day, is about 0.5 to about 30 mg. In other embodiments, each of the initial doses, per day, is about 0.5 to about 16 mg. In further embodiments, each of the initial doses, per day, is about 0.5 to about 8 mg. In yet other embodiments, each of the initial doses, per day, is about 0.5 to about 5 mg. In yet other embodiments, each of the initial doses, per day, is about 0.5 to about 4 mg. In still further embodiments, each of the initial doses, per day, is about 0.5 to about 2 mg. In other embodiments, each of the initial doses, per day, is about 0.5 to about 1 mg. In further embodiments, each of the initial doses, per day, is about 1 to about 8 mg. In yet other embodiments, each of the initial doses, per day, is about 1 to about 5 mg. In yet other embodiments, each of the initial doses, per day, is about 1 to about 4 mg. In still further embodiments, each of the initial doses, per day, is about 1 to about 2 mg.

Each of the subsequent doses may be the same or may differ. In some embodiments, the subsequent doses may be the same for a period of time during the method and then may change at another period of time during the method. In other embodiments, the subsequent doses may be the same during the entirety of the method. Thus, each of the subsequent doses per day, i.e., the subsequent daily dose, is, independently, at least about 0.1 mg. In some embodiments, the subsequent dose per day is at least about 0.1 mg. In further embodiments, the subsequent dose is at least about 0.5 mg, at least about 1 mg, at least about 1.5 mg, at least about 2 mg, at least about 3 mg, at least about 4 mg, at least about 5 mg, at least about 5.5 mg, at least about 6 mg, at least about 8 mg, at least about 16 mg, at least about 30 mg, or at least about 60 mg. In yet further embodiments, each subsequent dose per day is about 0.5 mg. In other embodiments, each subsequent dose per day is about 1 mg. In other embodiments, each subsequent dose per day is about 1.5 mg. In further embodiments, each subsequent dose per day is about 2 mg. In other embodiments, each subsequent dose per day is about 2.5 mg. In yet other embodiments, each subsequent dose per day is about 3 mg. In other embodiments, each subsequent dose per day is about 3.5 mg. In still further embodiments, each subsequent dose per day is about 4 mg. In other embodiments, each subsequent dose per day is about 4.5 mg. In other embodiments, each subsequent dose per day is about 5 mg. In further embodiments, each subsequent dose per day is about 5.5 mg. In still other embodiments, each subsequent dose per day is about 6 mg. In yet further embodiments, each subsequent dose per day is about 8 mg. In other embodiments, each subsequent dose per day is about 12.5 mg. In further embodiments, each subsequent dose per day is about 16 mg. In yet other embodiments, each subsequent dose per day is about 25 mg.

In some cases, the initial doses and the subsequent doses are the same. In some embodiments, the initial dose per day is about 1.5 mg, and the subsequent dose per day is about 1.5 mg. In other embodiments, the initial dose per day is about 1 mg, and the subsequent dose per day is about 1 mg. In further embodiments, the initial dose per day is about 2 mg, and the subsequent dose per day is about 2 mg.

In other embodiments, each of the subsequent doses, per day, is about 0.1 to about 100 mg. In further embodiments, each of the subsequent doses, per day, is about 0.5 to about 80 mg. In still other embodiments, each subsequent doses, per day, is about 0.5 to about 60 mg. In yet further embodiments, each of the subsequent doses, per day, is about 0.5 to about 30 mg. In other embodiments, each of the subsequent doses, per day, is about 0.5 to about 16 mg. In further embodiments, each of the subsequent doses, per day, is about 0.5 to about 8 mg. In yet other embodiments, each of the subsequent doses, per day, is about 0.5 to about 5 mg. In yet other embodiments, each of the subsequent doses, per day, is about 0.5 to about 4 mg. In still further embodiments, each of the subsequent doses, per day, is about 0.5 to about 2 mg. In other embodiments, each of the subsequent doses, per day, is about 0.5 to about 1 mg. In further embodiments, each of the subsequent doses, per day, is about 1 to about 8 mg. In yet other embodiments, each of the subsequent doses, per day, is about 1 to about 5 mg. In yet other embodiments, each of the subsequent doses, per day, is about 1 to about 4 mg. In still further embodiments, each of the subsequent doses, per day, is about 1 to about 2 mg.

In certain aspects, the disclosure provides methods for treating a human patient diagnosed with a cancer, comprising administering a therapeutically effective amount of a PRMT5 inhibitor, the method comprising (i) administering to the patient initial doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 days to about 20 days (e.g., about 7 days or about 14 days); and (ii) administering to the patient subsequent doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor for one or more subsequent dosing periods. In these methods, a first subsequent dosing period may be separated in time from the initial dosing period by at least about 5 days (e.g., about 7 days or about 10 days or about 14 days); and the subsequent dosing periods may be separated in time from each other by at least about 5 days (e.g., about 7 days or about 10 days or about 14 days).

In certain aspects, the disclosure provides methods for treating a human patient diagnosed with a cancer, comprising administering a therapeutically effective amount of a PRMT5 inhibitor, the method comprising (i) administering to the patient initial doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor that is (1 S,2R,3 S,5R)-3-(2-(2-amino-3-bromoquinolin-7-yl) ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 days to about 21 days (e.g., about 7 days or about 14 days); and (ii) administering to the patient subsequent doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor for one or more subsequent dosing periods. In these methods, a first subsequent dosing period may be separated in time from the initial dosing period by at least about 5 days (e.g., about 7 days or about 10 days or about 14 days); and the subsequent dosing periods may be separated in time from each other by at least about 5 days (e.g., about 7 days or about 10 days or about 14 days).

In other aspects, the disclosure provides methods for treating a human patient diagnosed with a cancer, comprising administering a therapeutically effective amount of a PRMT5 inhibitor, the method comprising (i) administering to the patient initial doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor that is (1 S,2R,3 S,5R)-3-(2-(2-amino-3-bromoquinolin-7-yl) ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 7 days to about 14 days (e.g., about 14 days); (ii) after the initial period, administering to the patient no doses of the PRMT5 inhibitor for an off-period of about 7 days to about 14 days (e.g., about 7 days); (iii) after the off-period, administering to the patient subsequent doses of at least about 0.1 mg (e.g., about 0.5 mg to about 5 mg, or about 0.5 mg to about 4 mg, or about 1 mg, about 1.5 mg, about 2 mg, about 2.5 mg, about 3 mg, about 3.5 mg, or about 4 mg, or about 4.5 mg, or about 5 mg, etc.) per day of the PRMT5 inhibitor for a subsequent dosing period of about 7 days to about 14 days (e.g., about 14 days); (iv) after the subsequent dosing period, administering to the patient no doses of the compound for an off-period of about 7 days to about 14 days (e.g., about 7 days); and optionally, sequentially repeating steps (iii) and (iv). For example, step (v) may comprise sequentially repeating steps (iii) and (iv) at least 2 times, at least 4 times, at least 6 times, at least 8 times, at least 10 times, at least 12 times, at least 14 times, at least 16 times, at least 18 times, at least 20 times, at least 22 times, at least 24 times, etc.

The term "subject" as used herein, refers to an animal, preferably a mammal, e.g., cat, dog, primate or human, more preferably a human, i.e., a "human patient" or "human subject", who is the object of treatment described herein.

The term "treatment", as used herein, is intended to refer to all processes wherein there may be a slowing, interrupting, arresting or stopping of the progression of a disease, but does not necessarily indicate a total elimination of all symptoms.

The term "compound of the disclosure" or "compound of the invention" as used herein refer to (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol of formula (I). This compound is also known as JNJ-64619178 and is discussed in International Patent Publication No. WO-2017/032840, which is incorporated by reference herein.

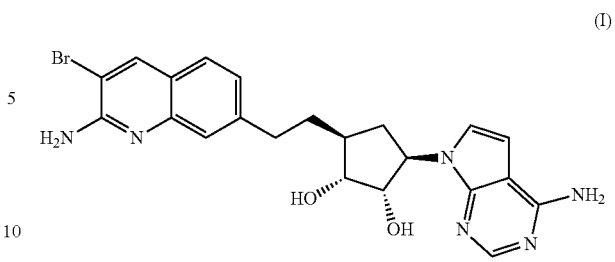

(I)

The compound may also exist in their tautomeric form. The term "tautomer" or "tautomeric form" refers to structural isomers of different energies which are interconvertible via a low energy barrier. Such forms in so far as they may exist are intended to be included within the scope of the present disclosure.

Where the stereochemistry of any particular chiral atom is not specified in the structures shown herein, then all stereoisomers are contemplated and included, either as a pure stereoisomer or as a mixture of two or more stereoisomers. As such, the compound described herein is meant to include stereoisomers and/or tautomers thereof. Thus, the compounds of the disclosure include all stereoisomers such as enantiomers, atropisomers, or diastereomers, racemates, E isomers, Z isomers, cis isomers, trans isomers, or and mixtures thereof.

Also contemplated are salts of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol. Pharmaceutically-acceptable salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g., in vacuo, by freeze-drying or by filtration). Salts may also be prepared by exchanging a counter-ion of a compound of the disclosure in the form of a salt with another counter-ion, for example using a suitable ion exchange resin.

Appropriate acids comprise, for example, inorganic acids such as hydrohalic acids, e.g., hydrochloric or hydrobromic acid, sulfuric, nitric, phosphoric and the like acids; or organic acids such as, for example, acetic, propanoic, hydroxyacetic, lactic, pyruvic, oxalic (i.e., ethanedioic), malonic, succinic (i.e., butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form. The compound or solvate thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g., the lithium, sodium, potassium, magnesium, calcium salts and the like, salts with organic bases, e.g., primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

Further contemplated are prodrugs of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a salt thereof. The term "prodrug" includes any compound that is metabolised in vivo to a form that compound in an experimentally-detectable amount. In some embodiments, prodrugs include compounds wherein a hydroxyl, amino, sulfhydryl, carboxy or carbonyl group in a compound is bonded to any group that may be cleaved in vivo to regenerate the free hydroxyl, amino, sulfhydryl, carboxy or carbonyl group, respectively. Examples of prodrugs include, but are not limited to, esters and carbamates of hydroxy functional groups, esters groups of carboxyl functional groups, N-acyl derivatives and N-Mannich bases. General information on prodrugs may be found, e.g., in Bundegaard, H. "Design of Prodrugs" p. 1-92, Elsevier, New York-Oxford (1985).

Also contemplated are solvates of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a salt thereof. The term "solvate" as used herein comprises hydrates and solvent addition forms which (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol is able to form, as well as pharmaceutically acceptable addition salts thereof. Examples of such forms are, e.g., hydrates, alcoholates and the like. In some embodiments, a solvate of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol is utilized. In other embodiments, a hydrate of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol is utilized.

The general preparation of the compound described herein is described in International Patent Publication No. WO-2017/032840 and in the specific examples, and is generally prepared from starting materials which are either commercially available or prepared by standard synthetic processes commonly used by those skilled in the art.

The methods described herein are useful for treating cancers. The cancer may be a solid cancer or a cancer affecting the blood, i.e., a hematological cancer. The term "solid cancer" as used herein refer to an abnormal cell growth that can present in a subject in solid organs. In some embodiments, the cancer is characterized by a splicing factor mutation, such as a myelodysplastic syndrome (MDS). In other embodiments, the cancer is a solid cancer. In further embodiments, the cancer is a hematological cancer. The cancer may be hormone-dependent or hormone-independent.

The cancer may be at any stage of progression in the subject. In some embodiments, the cancer is in an early or beginning stage, i.e., the tumor ("T") stage, and the cancer is localized. In other embodiments, the cancer is in an advanced stage, i.e., an advanced cancer. The term "advanced stage" as used herein may refer to a cancer that has spread to one or more areas of the body. Thus, in some aspects, the cancer is an advanced stage cancer that has spread to the lymph nodes and is known as the node ("N") stage, e.g., the node-positive ("N+") stage. In other aspects, the cancer is an advanced stage cancer that has spread to other parts of the body and is known as the metastasis ("M") stage Examples of cancers which may be treated include, but are not limited to, acoustic neuroma, adenocarcinoma, adenoid cystic carcinoma (ACC), adrenal gland cancer, anal cancer, angiosarcoma, appendix cancer, benign monoclonal gammopathy, biliary cancer, bladder cancer, breast cancer, brain cancer, bronchus cancer, carcinoid tumor, cervical cancer, chordoma, choriocarcinoma, craniopharyngioma, colorectal cancer, epithelial carcinoma, ependymoma, endothelio sarcoma, endometrial cancer, esophageal cancer, Ewing sarcoma, eye cancer, familiar hypereosinophilia, gall bladder cancer, gastric cancer, gastrointestinal stromal tumor, head and neck cancer, hematopoietic cancer, heavy chain disease, hemangioblastoma, inflammatory myofibroblastic tumor, immunocytic amyloidosis, kidney cancer, liver cancer, lung cancer, leiomyosarcoma, mastocytosis, myelodysplastic syndrome (MDS such as low risk and high risk MDS), mesothelioma, myeloproliferative disorder, neuroblastoma, neurofibroma, neuroendocrine cancer, osteosarcoma, ovarian cancer, papillary adenocarcinoma, parotid carcinoma, pancreatic cancer, penile cancer, pinealoma, primitive neuroectodermal tumor, prostate cancer, rectal cancer, rhabdomyosarcoma, salivary gland or duct cancer, skin cancer, small bowel cancer, soft tissue sarcoma, sebaceous gland carcinoma, sweat gland carcinoma, synovioma, testicular cancer, thyroid cancer, urethral cancer, vaginal cancer, or vulvar cancer. In some embodiments, the cancer is an angiosarcoma such as lymphangio sarcoma, lymphangioendothelio sarcoma, or hemangio sarcoma. In other embodiments, the cancer is a biliary cancer such as cholangiocarcinoma. In further embodiments, the cancer is a breast cancer such as an adenocarcinoma of the breast, papillary carcinoma of the breast, mammary cancer, or medullary carcinoma of the breast. In still further embodiments, the breast cancer is triple negative cancer (TNBC) In yet other embodiments, the cancer is a brain cancer such as a meningioma, glioma or medulloblastoma. Examples of gliomas include an astrocytoma or oligodendroglioma. In still further embodiments, the cancer is a cervical cancer such as a cervical adenocarcinoma. In other embodiments, the cancer is a colorectal cancer such as a colon cancer, rectal cancer, or a colorectal adenocarcinoma. In further embodiments, the cancer is an endothelio sarcoma such as Kaposi's sarcoma or a multiple idiopathic hemorrhagic sarcoma. In still other embodiments, the cancer is an endometrial cancer such as a uterine cancer or a uterine sarcoma. In yet further embodiments, the cancer is an esophageal cancer such as an adenocarcinoma of the esophagus or Barrett's adenocarcinoma. In other embodiments, the cancer is an eye cancer such as an intraocular melanoma or retinoblastoma. In some aspects, the intraocular melanoma is uveal melanoma. In further embodiments, the cancer is a gastric cancer such as a stomach adenocarcinoma. In yet other embodiments, the cancer is a head and neck cancer such as a head and neck squamous cell carcinoma. In still further embodiments, the cancer is an oral cancer such as oral squamous cell carcinoma. In further embodiments, the cancer is a parotid carcinoma. In other embodiments, the cancer is a throat cancer such as pharyngeal cancer, laryngeal cancer, nasopharyngeal cancer, or oropharyngeal cancer. In further embodiments, the cancer is a hematopoietic cancer. Examples of hematopoietic cancers include leukemias, lymphomas, myeloproliferative neoplasms (MPN), and multiple myeloma. Examples of leukemias include acute lymphocytic leukemia, acute myelocytic leukemia, chronic myelocytic leukemia, chronic myelomonocytic leukemia (CMML), or chronic lymphocytic leukemia. Examples of lymphomas include Hodgkin lymphoma and non-Hodgkin lymphoma (NHL). In some embodiments, the cancer is non-Hodgkin lymphoma. In other examples, the cancer is MDS. In further examples, the cancer is multiple myeloma.

Examples of lymphomas include B-cell NHL. Examples of acute lymphocytic leukemias include B-cell ALL, and T-cell ALL. Examples of acute myelocytic leukemia (AML) includes B-cell AML, or T-cell AML, including low- and high-risk AML. Examples of chronic myelocytic leukemia (CIVIL) include B-cell CIVIL or T-cell CML. Examples of chronic lymphocytic leukemia (CLL) include B-cell CLL or T-cell CLL. Examples of Hodgkin lymphomas (HL) include B-cell HL and T-cell HL. Examples of non-Hodgkin lymphomas (NHL) include B-cell NHL and T-cell NHL. Examples of B-cell NHL include diffuse large cell lymphoma, follicular lymphoma, chronic lymphocytic leukemia/small lymphocytic lymphoma, mantle cell lymphoma, marginal zone B-cell lymphomas, primary mediastinal B-cell lymphoma, Burkitt lymphoma, lymphoplasmacytic lymphoma, immunoblastic large cell lymphoma, hairy cell leukemia, precursor B-Iymphoblastic lymphoma and primary central nervous system lymphoma; and T-cell NHL such as precursor T-lymphoblastic lymphoma/leukemia, peripheral T-cell lymphoma, or multiple myeloma. Examples of diffuse large cell lymphoma include diffuse large B-cell lymphoma (DLBCL). Examples of peripheral T-cell lymphoma include cutaneous T-cell lymphoma, angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma. Examples of cutaneous T-cell lymphoma such as mycosis fungiodes or Sezary syndrome. Examples of marginal zone B-cell lymphoma include mucosa-associated lymphoid tissue lymphomas, nodal marginal zone B-cell lymphoma, or splenic marginal zone B-cell lymphoma. Examples of heavy chain disease include alpha chain disease, gamma chain disease, or mu chain disease. Examples of T-cell NHL include precursor T-lymphoblastic lymphoma/leukemia, and peripheral T-cell lymphoma.

In still other embodiments, the cancer is a heavy chain disease such as alpha chain disease, gamma chain disease, or mu chain disease. In further embodiments, the cancer is a kidney cancer such as nephroblastoma, i.e., Wilms' tumor or renal cell carcinoma. In still other embodiments, the cancer is a liver cancer such as hepatocellular cancer or malignant hepatoma. In yet further embodiments, the cancer is a lung cancer such as bronchogenic carcinoma, non-small cell lung cancer (NSCLC), squamous lung cancer, adenocarcinoma of the lung, Lewis lung carcinoma, lung neuroendocrine tumors, typical carcinoid, atypical carcinoid, small cell lung cancer, or large cell neuroendocrine carcinoma. In some aspects, the cancer is a small cell lung cancer (SCLC). In other embodiments, the cancer is a myeloproliferative disorder such as polycythemia Vera, essential thrombocytosis, agnogenic myeloid metaplasia a.k.a. myelofibrosis (MF), chronic idiopathic myelofibrosis, chronic myelocytic leukemia, chronic neutrophilic leukemia, or hypereosinophilic syndrome. In other embodiments, the cancer is a neurofibroma such as neurofibromatosis type 1 or type 2 or schwannomatosis. In still other embodiments, the cancer is a neuroendocrine cancer such as a gastroenteropancreatic neuroendocrine tumor or carcinoid tumor. In further embodiments, the cancer is an ovarian cancer such as a cystadenocarcinoma, ovarian embryonal carcinoma, or ovarian adenocarcinoma. In other embodiments, the cancer is a pancreatic cancer such as pancreatic adenocarcinoma, intraductal papillary mucinous neoplasm, or Islet cell tumor. In further embodiments, the cancer is a penile cancer such as Paget's disease of the penis and scrotum, pinealoma, or a primitive neuroectodermal tumor. In still other embodiments, the cancer is a prostate cancer such as prostate adenocarcinoma. In yet further embodiments, the cancer is a skin cancer such as squamous cell carcinoma, keratoacanthoma, melanoma, or basal cell carcinoma. In further embodiments, the cancer is a salivary cancer such as pleomorphic adenoma, mucoepidermoid carcinoma, and acinic cell carcinoma. In other embodiments, the cancer is a small bowel cancer such as appendix cancer. In further embodiments, the cancer is a soft tissue sarcoma such as malignant fibrous histiocytoma, liposarcoma, malignant peripheral nerve sheath tumor, chondrosarcoma, fibrosarcoma, or myxosarcoma. In yet other embodiments, the cancer is a testicular cancer such as a seminoma or testicular embryonal carcinoma). In still further embodiments, the cancer is a thyroid cancer such as a papillary carcinoma of the thyroid, papillary thyroid carcinoma, or medullary thyroid cancer. In other embodiments, the cancer is a vulvar cancer such as Paget's disease of the vulva. In further embodiments, the cancer is a clear cell carcinoma, oncocytic carcinoma, or polymorphous adenocarcinoma.

In some embodiments, the methods are useful in treating breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma (HNSCC), brain tumors, hepatocellular carcinoma, renal cell carcinoma, melanoma, oligodendroglioma, ovarian clear cell carcinoma, uveal melanoma, prostate cancer, and ovarian serous cystadenoma.

In other embodiments, methods are useful in reducing the risk of cancer recurrence.

The methods described herein permit administration of the PRMT5 inhibitor via any acceptable route. In some embodiments, the PRMT5 inhibitor is administered orally, parenterally (i.e., in the form of a liquid), rectally (i.e., in the form of a suppository), topically (i.e., in the form of a transdermal patch, ointment, or cream), or intranasally. Examples of parenteral administration include intravenous (IV), intramuscular (IM), and subcutaneous (SC) injection. Preferably, the PRMT5 inhibitor is administered orally. In other embodiments, the PRMT5 inhibitor is administered orally. In further embodiments, the PRMT5 inhibitor is administered parenterally.

While it is possible for the active ingredient to be administered alone, i.e., neat, it may also be present in pharmaceutical composition. Accordingly, the present disclosure further provides a pharmaceutical composition and, as active ingredient, the PRMT5 inhibitor described herein. As such the PRMT5 inhibitor may be formulated into various pharmaceutical forms for administration purposes.

When the PRMT5 inhibitor is formulated in a pharmaceutical composition, the composition also comprises a pharmaceutically acceptable carrier, diluent, and/or excipient. The particular carrier, diluent, and/or excipient will depend on the route of administration and may be determined by those skilled in the art. The carrier, diluent, and/or excipient must be "acceptable" in the sense of being compatible with the other ingredients of the composition and not deleterious to the recipients thereof. Examples of excipients include diluents, lubricants, binders, and disintegrating agents. suspending agents, penetration enhancing agent and/or a suitable wetting agent. The excipient may be in the form of a liquid such as water, a glycol, an oil, or an alcohol or a solid such as a starch, sugar, or kaolin.

Pharmaceutical compositions designed for oral administration may be in the form of solid or liquid. In some embodiments, the oral formulation is a liquid preparation such as a suspension, syrup, elixir, emulsion, or solution. In other embodiments, the oral formulation is a solid preparation such as a tablet (including scored or coated tablets), capsule, caplet (including scored or coated caplets), pill, powder, or wafer.

To prepare the pharmaceutical compositions, an effective amount of the particular compound as the active ingredient is combined with a pharmaceutically acceptable carrier. Liquid solutions may be prepared in which the carrier comprises, e.g., saline solution, glucose solution, oils, or a mixture thereof such as a mixture of saline and glucose solution. Appropriate oils include, without limitation, peanut oil, sesame oil, cottonseed oil, corn oil, soybean oil, synthetic glycerol esters of long chain fatty acids and mixtures of these and other oils.

The compounds, that can be suitable to treat or prevent cancer or cancer-related conditions, may be administered alone or in combination with one or more additional therapeutic agents. Combination therapy includes administration of a single pharmaceutical dosage formulation which contains the compound described herein, a pharmaceutically acceptable addition salt, or a solvate thereof, and one or more additional therapeutic agents, as well as administration of the PRMT5 inhibitor and each additional therapeutic agents in its own separate pharmaceutical dosage formulation. For example, the PRMT5 inhibitor and a therapeutic agent may be administered to the patient together in a single oral dosage composition such as a tablet or capsule, or each agent may be administered in separate oral dosage formulations.

For use in the methods described herein, the compounds may be administered in conjunction with an adjuvant therapy. The term "adjuvant therapy" as used herein refers to the administration of one or more other medicinal agents, more particularly, with other chemotherapeutics, or techniques that can be used in cancer therapy. In some embodiments, the adjuvant therapy comprises radiation. In other embodiments, the adjuvant therapy comprises a chemotherapeutic agent. In further embodiments, the chemotherapeutic agent is a DNA methyl transferase inhibitor such as 5-azacitidine or decitabine. In still other embodiments, the chemotherapeutic agent is 5-azacitidine.

Embodiments

Embodiment 1

A PRMT5 (protein arginine methyltransferase 5) inhibitor for use in treating a human patient diagnosed with a cancer by administration of a therapeutically effective amount of the PRMT5 inhibitor to the human patient, wherein the administration comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days.

Embodiment 2

A PRMT5 (protein arginine methyltransferase 5) inhibitor for use in a method of treating a human patient diagnosed with a cancer, wherein the method comprises administering a therapeutically effective amount of the PRMT5 inhibitor to the human patient, wherein the method comprises: (i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and (ii) administering to the patient subsequent doses of at least about 0.1 mg per day of the PRMT5 inhibitor for one or more subsequent dosing periods of about 5 to about 20 days each; wherein, a first subsequent dosing period is separated in time from the initial dosing period by at least about 5 days; and the subsequent dosing periods are separated in time from each other by at least about 5 days. Embodiment 4. The PRMT5 inhibitor for use according to any one of the preceding embodiments, wherein each of the initial dose per day or subsequent dose per day is, independently, at least about 0.5 mg, at least about 1 mg, at least about 2 mg, at least about 3 mg, at least about 4 mg, at least about 5 mg, at least about 5.5 mg, at least about 6 mg, at least about 8 mg, at least about 16 mg, at least about 30 mg, or at least about 60 mg.

Embodiment 5

The PRMT5 inhibitor for use according to any one of the preceding embodiments, wherein each of the initial dose per day or subsequent dose per day is, independently, about 0.1 to about 100 mg, about 0.5 to about 80 mg, about 0.5 to about 60 mg, 0.5 to about 30 mg, about 0.5 to about 16 mg, about 0.5 to about 8 mg, about 0.5 to about 4 mg, about 0.5 to about 2 mg, or about 0.5 to about 1 mg.

Embodiment 6

The PRMT5 inhibitor for use according to any one of the preceding embodiments, wherein each of the initial dose per day and subsequent dose per day is, independently, about 0.5 mg, about 1 mg, about 2 mg, about 3 mg, about 4 mg, about 5 mg, about 5.5 mg, about 6 mg, about 8 mg, about 12.5 mg, about 16 mg, about 25 mg, about 30 mg, about 50 mg, about 60 mg, about 100 mg, about 200 mg, about 400 mg, about 600 mg, about 800 mg, or about 1200 mg.

Embodiment 7

The PRMT5 inhibitor for use according to any one of the preceding embodiments, wherein each of the initial dose or at least one subsequent dose is administered once daily or both the initial dose and at least one subsequent dose are administered once daily.

Embodiment 8

The PRMT5 inhibitor for use according to any one of the preceding embodiments, wherein each of the initial dose or at least one subsequent dose is administered twice daily (BID) in divided doses or both the initial dose and at least one subsequent dose are administered twice daily in divided doses.

Embodiment 9

The PRMT5 inhibitor for use according to embodiment 8, wherein the divided doses are equal.

Embodiment 10

The PRMT5 inhibitor for use according to any one of the preceding embodiments, wherein the initial dosing period is about 7 days to about 14 days.

Embodiment 11

The PRMT5 inhibitor for use according to any one of the preceding embodiments, wherein the initial dosing period is about 7 days.

Embodiment 12

The PRMT5 inhibitor for use according to any one of embodiments 1-11, wherein the initial dosing period is about 14 days.

Embodiment 13

The PRMT5 inhibitor for use according to any one of the preceding embodiments, wherein the first subsequent dosing period is separated in time from the initial dosing period by at least about 7 days; and the subsequent dosing periods are separated in time from each other by at least about 7 days.

Embodiment 14

The PRMT5 inhibitor for use according to any one of the preceding embodiments, wherein the first subsequent dosing period is separated in time from the initial dosing period by about 7 days; and the subsequent dosing periods are separated in time from each other by about 7 days.

Embodiment 15

The PRMT5 inhibitor for use according to any one of embodiments 1 to 12, wherein each subsequent dosing period is about 7 days to about 14 days.

Embodiment 16

The PRMT5 inhibitor for use according to any one of the preceding embodiments, wherein each subsequent dosing period is about 7 days.

Embodiment 17

The PRMT5 inhibitor for use according to any one of embodiments 1 to 15, wherein each subsequent dosing period is about 14 days.

Embodiment 18

The PRMT5 inhibitor for use according to any one of the preceding embodiments, wherein the initial dose or at least one subsequent dose is administered orally or the initial dose and at least one subsequent dose are administered orally.

Embodiment 19

The PRMT5 inhibitor for use according to any one of the preceding embodiments, wherein the initial dose and at least one subsequent dose are the same.

Embodiment 20

The PRMT5 inhibitor for use according to any one of embodiments 1 to 18, wherein the initial dose and at least one subsequent dose are different.

Embodiment 21

The PRMT5 inhibitor for use according to any one of the preceding embodiments, wherein the cancer is an advanced cancer.

Embodiment 22

The PRMT5 inhibitor for use according to any one of the preceding embodiments, wherein the cancer is acoustic neuroma, adenocarcinoma, adenoid cystic carcinoma, adrenal gland cancer, anal cancer, angiosarcoma, appendix cancer, benign monoclonal gammopathy, biliary cancer, bladder cancer, breast cancer, brain cancer, bronchus cancer, carcinoid tumor, cervical cancer, chordoma, choriocarcinoma, craniopharyngioma, colorectal cancer, epithelial carcinoma, ependymoma, endothelio sarcoma, endometrial cancer, esophageal cancer, Ewing sarcoma, eye cancer, familiar hypereosinophilia, gall bladder cancer, gastric cancer, gastrointestinal stromal tumor, head and neck cancer, hematopoietic cancer, heavy chain disease, hemangioblastoma, inflammatory myofibroblastic tumor, immunocytic amyloidosis, kidney cancer, liver cancer, lung cancer, leiomyosarcoma, mastocytosis, myelodysplastic syndrome, mesothelioma, myeloproliferative disorder, neuroblastoma, neurofibroma, neuroendocrine cancer, osteosarcoma, ovarian cancer, papillary adenocarcinoma, pancreatic cancer, penile cancer, pinealoma, primitive neuroectodermal tumor, prostate cancer, rectal cancer, rhabdomyosarcoma, salivary gland cancer, skin cancer, small bowel cancer, soft tissue sarcoma, sebaceous gland carcinoma, sweat gland carcinoma, synovioma, testicular cancer, thyroid cancer, urethral cancer, vaginal cancer, or vulvar cancer.

Embodiment 23

The PRMT5 inhibitor for use according to any one of the preceding embodiments, wherein the cancer is a solid cancer.

Embodiment 24

The PRMT5 inhibitor for use according to any one of the preceding embodiments, wherein the cancer is a non-small cell lung cancer.

Embodiment 25

The PRMT5 inhibitor for use according to any one of embodiments 1 to 22, wherein the cancer is a hematopoietic cancer.

Embodiment 26

The PRMT5 inhibitor for use according to embodiment 25, wherein the cancer is non-Hodgkin's lymphoma.

Embodiment 27

The PRMT5 inhibitor for use according to any one of the preceding embodiments, further comprising administering an adjuvant therapy to the patient.

Embodiment 28

The PRMT5 inhibitor for use according to embodiment 27, wherein the adjuvant therapy comprises administering radiation to the patient.

Embodiment 29

The PRMT5 inhibitor for use according to embodiment 27, wherein the adjuvant therapy comprises administering an effective amount of a chemotherapeutic agent to the patient.

Embodiment 30

The PRMT5 inhibitor for use according to embodiment 29, wherein the chemotherapeutic agent is a DNA methyl transferase inhibitor such as 5-azacitidine or decitabine, preferably 5-azacitidine.

Embodiment 31

The PRMT5 inhibitor for use according to any one of the preceding embodiments, wherein efficacy is measured by determining a patient time to disease progression or a patient response rate.

Embodiment 32

The PRMT5 inhibitor for use according to any one of the preceding embodiments, wherein the compound is a pharmaceutically acceptable addition salt of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Embodiment 33

The PRMT5 inhibitor for use according to any one of embodiments 1 to 32, wherein the compound is a solvate of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Embodiment 34

The PRMT5 inhibitor for use according to embodiment 33, wherein the solvate is a hydrate.

Embodiment 35

The PRMT5 inhibitor for use according to any one of embodiments 1 to 32, wherein the compound is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Embodiment 36

A PRMT5 (protein arginine methyltransferase 5) inhibitor for use in treating a human patient diagnosed with a cancer by administration of a therapeutically effective amount of the PRMT5 inhibitor to the human patient, wherein the administration comprises:
(i) administering to the patient initial doses of about 0.1 mg to about 5 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days; and
(ii) administering to the patient subsequent doses of about 0.1 mg to about 5 mg per day of the PRMT5 inhibitor for one or more subsequent dosing periods;
wherein:
a first subsequent dosing period is separated in time from the initial dosing period by at least about 7 days; and
the subsequent dosing periods are separated in time from each other by at least about 7 days.

Embodiment 37

A PRMT5 (protein arginine methyltransferase 5) inhibitor for use in treating a human patient diagnosed with a cancer by administration of a therapeutically effective amount of the PRMT5 inhibitor to the human patient, wherein the administration comprises:
(i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 7 days to about 14 days;
(ii) after the initial period, administering to the patient no doses of the PRMT5 inhibitor for an off-period of about 7 days to about 14 days;
(iii) after the off-period, administering to the patient subsequent doses of at least about 0.1 mg per day of the PRMT5 inhibitor for a subsequent dosing period of about 7 days to about 14 days;
(iv) after the subsequent dosing period, administering to the patient no doses of the compound for an off-period of about 7 days to about 14 days; and
(v) optionally, sequentially repeating steps (iii) and (iv).

Embodiment 38

The PRMT5 inhibitor for use according to embodiment 37, comprising:
(i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 14 days;
(ii) after the initial period, administering to the patient no doses of the PRMT5 inhibitor for an off-period of about 7 days;
(iii) after the off-period, administering to the patient subsequent doses of at least about 0.1 mg per day of the PRMT5 inhibitor for a subsequent dosing period of about 14 days;
(iv) after the subsequent dosing period, administering to the patient no doses of the compound for an off-period of about 7 days; and
(v) optionally, sequentially repeating steps (iii) and (iv).

Embodiment 39

The PRMT5 inhibitor for use according to embodiment 37, comprising:
(i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 7 days;
(ii) after the initial period, administering to the patient no doses of the PRMT5 inhibitor for an off-period of about 7 days;
(iii) after the off-period, administering to the patient subsequent doses of at least about 0.1 mg per day of the PRMT5 inhibitor for a subsequent dosing period of about 7 days;
(iv) after the subsequent dosing period, administering to the patient no doses of the compound for an off-period of about 7 days; and
(v) optionally, sequentially repeating steps (iii) and (iv).

Embodiment 40

The PRMT5 inhibitor for use according to any one of embodiments 37-39, wherein step (v) comprises sequentially repeating steps (iii) and (iv) at least 4 times.

Embodiment 41

The PRMT5 inhibitor for use according to any one of embodiments 37-40 comprising administering to the patient the initial doses of about 0.5 mg to about 5 mg per day of the PRMT5 inhibitor, and administering to the patient the subsequent doses of about 0.5 mg to about 5 mg per day of the PRMT5 inhibitor.

Embodiment 42

The PRMT5 inhibitor for use according to any one of embodiments 37-41, wherein the method is effective in reducing a tumor volume in the patient.

Aspects

Aspect 1. A method for treating a human patient diagnosed with a cancer, comprising administering a therapeutically effective amount of a PRMT5 (protein arginine methyltransferase 5) inhibitor, the method comprising:
(i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 5 to about 20 days; and
(ii) administering to the patient subsequent doses of at least about 0.1 mg per day of the PRMT5 inhibitor for one or more subsequent dosing periods of about 5 to about 20 days each;
wherein:
a first subsequent dosing period is separated in time from the initial dosing period by at least about 5 days; and
the subsequent dosing periods are separated in time from each other by at least about 5 days.

Aspect 3. The method of Aspect 1, wherein each of the initial dose per day or subsequent dose per day is, independently, at least about 0.5 mg, at least about 1 mg, at least about 2 mg, at least about 3 mg, at least about 4 mg, at least about 5 mg, at least about 5.5 mg, at least about 6 mg, at least about 8 mg, at least about 16 mg, at least about 30 mg, or at least about 60 mg.

Aspect 4. The method of any one of the preceding Aspects, wherein each of the initial dose per day or subsequent dose per day is, independently, about 0.1 to about 100 mg, about 0.5 to about 80 mg, about 0.5 to about 60 mg, 0.5 to about 30 mg, about 0.5 to about 16 mg, about 0.5 to about 8 mg, about 0.5 to about 4 mg, about 0.5 to about 2 mg, or about 0.5 to about 1 mg.

Aspect 5. The method of any one of the preceding Aspects, wherein each of the initial dose per day and subsequent dose per day is, independently, about 0.5 mg, about 1 mg, about 2 mg, about 3 mg, about 4 mg, about 5 mg, about 5.5 mg, about 6 mg, about 8 mg, about 12.5 mg, about 16 mg, about 25 mg, about 30 mg, about 50 mg, about 60 mg, about 100 mg, about 200 mg, about 400 mg, about 600 mg, about 800 mg, or about 1200 mg.

Aspect 6. The method of any one of the preceding Aspects, wherein each of the initial dose or at least one subsequent dose is administered once daily or both the initial dose and at least one subsequent dose are administered once daily.

Aspect 7. The method of any one of Aspects 1 to 5, wherein each of the initial dose or at least one subsequent dose is administered twice daily (BID) in divided doses or both the initial dose and at least one subsequent dose are administered twice daily in divided doses.

Aspect 8. The method of Aspect 7, wherein the divided doses are equal.

Aspect 9. The method of any one of the preceding Aspects, wherein the initial dosing period is about 7 days to about 14 days.

Aspect 10. The method of any one of the preceding Aspects, wherein the initial dosing period is about 7 days.

Aspect 11. The method of any one of Aspects 1 to 9, wherein the initial dosing period is about 14 days.

Aspect 12. The method of any one of the preceding Aspects, wherein the first subsequent dosing period is separated in time from the initial dosing period by at least about 7 days; and the subsequent dosing periods are separated in time from each other by at least about 7 days.

Aspect 13. The method of any one of the preceding Aspects, wherein the first subsequent dosing period is separated in time from the initial dosing period by about 7 days; and the subsequent dosing periods are separated in time from each other by about 7 days.

Aspect 14. The method of any one of Aspects 1 to 11, wherein each subsequent dosing period is about 7 days to about 14 days.

Aspect 15. The method of any one of the preceding Aspects, wherein each subsequent dosing period is about 7 days.

Aspect 16. The method of any one of Aspects 1 to 14, wherein each subsequent dosing period is about 14 days.

Aspect 17. The method of any one of the preceding Aspects, wherein the initial dose or at least one subsequent dose is administered orally or the initial dose and at least one subsequent dose are administered orally.

Aspect 18. The method of any one of the preceding Aspects, wherein the initial dose and at least one subsequent dose are the same.

Aspect 19. The method of any one of Aspects 1 to 17, wherein the initial dose and at least one subsequent dose are different.

Aspect 20. The method of any one of the preceding Aspects, wherein the cancer is an advanced cancer.

Aspect 21. The method of any one of the preceding Aspects, wherein the cancer is acoustic neuroma, adenocarcinoma, adenoid cystic carcinoma, adrenal gland cancer, anal cancer, angiosarcoma, appendix cancer, benign monoclonal gammopathy, biliary cancer, bladder cancer, breast cancer, brain cancer, bronchus cancer, carcinoid tumor, cervical cancer, chordoma, choriocarcinoma, craniopharyngioma, colorectal cancer, epithelial carcinoma, ependymoma, endothelio sarcoma, endometrial cancer, esophageal cancer, Ewing sarcoma, eye cancer, familiar hypereosinophilia, gall bladder cancer, gastric cancer, gastrointestinal stromal tumor, head and neck cancer, hematopoietic cancer, heavy chain disease, hemangioblastoma, inflammatory myofibroblastic tumor, immunocytic amyloidosis, kidney cancer, liver cancer, lung cancer, leiomyosarcoma, mastocytosis, myelodysplastic syndrome, mesothelioma, myeloproliferative disorder, neuroblastoma, neurofibroma, neuroendocrine cancer, osteosarcoma, ovarian cancer, papillary adenocarcinoma, pancreatic cancer, penile cancer, pinealoma, primitive neuroectodermal tumor, prostate cancer, rectal cancer, rhabdomyosarcoma, salivary gland cancer, skin cancer, small bowel cancer, soft tissue sarcoma, sebaceous gland carcinoma, sweat gland carcinoma, synovioma, testicular cancer, thyroid cancer, urethral cancer, vaginal cancer, or vulvar cancer.

Aspect 22. The method of any one of the preceding Aspects, wherein the cancer is a solid cancer.

Aspect 23. The method of any one of the preceding Aspects, wherein the cancer is a non-small cell lung cancer.

Aspect 24. The method of any one of Aspects 1 to 21, wherein the cancer is a hematopoietic cancer.

Aspect 25. The method of Aspect 24, wherein the cancer is non-Hodgkin's lymphoma.

Aspect 26. The method of any one of the preceding Aspects, further comprising administering an adjuvant therapy to the patient.

Aspect 27. The method of Aspect 26, wherein the adjuvant therapy comprises administering radiation to the patient.

Aspect 28. The method of Aspect 26, wherein the adjuvant therapy comprises administering an effective amount of a chemotherapeutic agent to the patient.

Aspect 29. The method of Aspect 28, wherein the chemotherapeutic agent is a DNA methyl transferase inhibitor such as 5-azacitidine or decitabine, preferably 5-azacitidine.

Aspect 30. The method of any one of the preceding Aspects, wherein efficacy is measured by determining a patient time to disease progression or a patient response rate.

Aspect 31. The method of any one of the preceding Aspects, wherein the compound is a pharmaceutically acceptable addition salt of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Aspect 32. The method of any one of Aspects 1 to 31, wherein the compound is a solvate of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Aspect 33. The method of Aspect 32, wherein the solvate is a hydrate.

Aspect 34. The method of any one of Aspects 1 to 31, wherein the compound is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

Aspect 35. A method for treating a human patient diagnosed with a cancer, comprising administering a therapeutically effective amount of a PRMT5 (protein arginine methyltransferase 5) inhibitor, the method comprising:
(i) administering to the patient initial doses of about 0.1 mg to about 5 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days; and
(ii) administering to the patient subsequent doses of about 0.1 mg to about 5 mg per day of the PRMT5 inhibitor for one or more subsequent dosing periods;
wherein:
a first subsequent dosing period is separated in time from the initial dosing period by at least about 7 days; and
the subsequent dosing periods are separated in time from each other by at least about 7 days.

Aspect 36. A method for treating a human patient diagnosed with a cancer, comprising administering a therapeutically effective amount of a PRMT5 (protein arginine methyltransferase 5) inhibitor, the method comprising:
(i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 7 days to about 14 days;
(ii) after the initial period, administering to the patient no doses of the PRMT5 inhibitor for an off-period of about 7 days to about 14 days;
(iii) after the off-period, administering to the patient subsequent doses of at least about 0.1 mg per day of the PRMT5 inhibitor for a subsequent dosing period of about 7 days to about 14 days;
(iv) after the subsequent dosing period, administering to the patient no doses of the compound for an off-period of about 7 days to about 14 days; and
(v) optionally, sequentially repeating steps (iii) and (iv).

Aspect 37. The method of Aspect 36 comprising:
(i) administering to the patient initial doses of at least about 0.1 mg per day of the PRMT5 inhibitor that is (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol or a pharmaceutically acceptable addition salt or solvate thereof for an initial dosing period of about 14 days;
(ii) after the initial period, administering to the patient no doses of the PRMT5 inhibitor for an off-period of about 7 days;
(iii) after the off-period, administering to the patient subsequent doses of at least about 0.1 mg per day of the PRMT5 inhibitor for a subsequent dosing period of about 14 days;
(iv) after the subsequent dosing period, administering to the patient no doses of the compound for an off-period of about 7 days; and
(v) optionally, sequentially repeating steps (iii) and (iv).

Aspect 38. The method of Aspect 36 comprising:
(i) administering to the patient initial doses of at least about 0.1 mg per day of the PRMT5 inhibitor that is (1S,2R,3S,5R)-3-(2-(2-amino-3-bromoquinolin-7-yl)

ethyl)-5-(4-amino-7H-pyrrolo[2,3-d]pyrimidin-7-yl)
cyclopentane-1,2-diol or a pharmaceutically acceptable
addition salt or solvate thereof for an initial dosing
period of about 7 days;

(ii) after the initial period, administering to the patient no doses of the PRMT5 inhibitor for an off-period of about 7 days;

(iii) after the off-period, administering to the patient subsequent doses of at least about 0.1 mg per day of the PRMT5 inhibitor for a subsequent dosing period of about 7 days;

(iv) after the subsequent dosing period, administering to the patient no doses of the compound for an off-period of about 7 days; and (v) optionally, sequentially repeating steps (iii) and (iv).

Aspect 39. The method according to any of Aspects 36-38, wherein step (v) comprises sequentially repeating steps (iii) and (iv) at least 4 times.

Aspect 40. The method according to any of Aspects 36-39 comprising administering to the patient the initial doses of about 0.5 mg to about 5 mg per day of the PRMT5 inhibitor and administering to the patient the subsequent doses of about 0.5 mg to about 5 mg per day of the PRMT5 inhibitor.

Aspect 41. The method according to any of Aspects 36-40, wherein the method is effective in reducing a tumor volume in the patient.

ABBREVIATIONS

| | |
|---|---|
| β-hCG | β human chorionic gonadotropin |
| $^{18}$F-FDG | 18F-fluorodeoxyglucose |
| 2D | 2-dimensional |
| ADL | activities of daily living |
| ALT | alanine aminotransferase |
| ALP | alkaline phosphatase; |
| AML | acute myeloid leukemia |
| Arg | arginine |
| AST | aspartate aminotransferase |
| AUC | area under the plasma concentration versus time curve |
| B cell | B lymphocyte |
| BCRP | breast cancer resistance protein |
| BLRM | Bayesian logistic regression model |
| C | cycle |
| CL/F | apparent total systemic clearance of drug after extravascular administration |
| $C_{max}$ | maximum observed plasma concentration |
| $C_{min}$ | minimum observed plasma concentration |
| CNS | central nervous system |
| CR | complete response |
| CSR | clinical study report |
| CT | computed tomography |
| D or d | day |
| DLBCL | diffuse large B-cell lymphoma |
| DLT | dose-limiting toxicity |
| DNA | deoxyribonucleic acid |
| DOR | duration of response |
| ECG | electrocardiogram |
| ECHO | echocardiogram |
| ECOG | Eastern Cooperative Oncology Group |
| EOT | end-of-treatment |
| EWOC | escalation with overdose control (principle) |
| ESA | erythropoiesis-stimulating agent |
| FDA | Food and Drug Administration (US) |
| FDG | $^{18}$F-fludeoxyglucose |
| FFPE | formalin-fixed, paraffin-embedded |
| FIH | first-in-human |
| FL | follicular lymphoma |
| GCP | good clinical practice |
| GGT | gamma-glutamyl transpeptidase; |
| GI | gastrointestinal |
| $GI_{50}$ | growth inhibition of 50% |
| HBsAg | hepatitis B surface antigen |
| HCV | hepatitis C virus |
| HP-β-CD | hydroxypropyl-β-cyclodextrin |

ABBREVIATIONS -continued

| | |
|---|---|
| HNSTD | highest non-severely toxic dose |
| ICF | informed consent form |
| IEC | Independent Ethics Committee |
| IPSS | International Prognostic Scoring System |
| IRB | Institutional Review Board |
| IV | intravenous |
| IWG | International Working Group |
| MAD | maximum administered dose |
| MCL | mantle cell lymphoma |
| mCRM | modified continual reassessment method |
| MDS | myelodysplastic syndromes |
| MRI | magnetic resonance imaging |
| mRNA | messenger ribonucleic acid |
| MTD | maximum tolerated dose |
| MUGA | multigated acquisition (scan) |
| NCI CTCAE | National Cancer Institute Common Terminology Criteria for Adverse Events |
| NHL | non-Hodgkin lymphoma |
| NOAEL | no observed adverse effect level |
| NOS | not otherwise specified |
| NSCLC | non-small cell lung cancer |
| PET | positron emission tomography |
| PD | pharmacodynamics |
| PK | pharmacokinetics |
| P-gp | P-glycoprotein |
| PQC | product quality complaint |
| PR | partial response |
| PRMT5 | protein arginine methyltransferase 5 |
| QD | daily |
| $R_A$ | accumulation index |
| RBC | red blood cell |
| RECIST | Response Criteria in Solid Tumors |
| RNA | ribonucleic acid |
| RP2D | recommended Phase 2 dose |
| SAM | S-adenosylmethionine |
| SCLC | small cell lung cancer |
| SDMA | symmetric dimethyl-arginine |
| SET | study evaluation team |
| SIPPM | site investigational product and procedures manual |
| SmD1/3-Me$_2$ | symmetrically di-methylated |
| SUSAR | suspected unexpected serious adverse reaction |
| $T_{1/2}$ | half-life |
| TLS | tumor lysis syndrome |
| TCR | T cell receptor |
| TGI | tumor growth inhibition |
| TI | transfusion independence |
| $T_{max}$ | time corresponding to the last quantifiable plasma concentration |
| TTR | time to response |
| ULN | upper limit of normal |
| UV | ultraviolet |
| Vss/F | volume of distribution at steady state |
| WHO | World Health Organization |

EXAMPLES

Example 1. Drug Substance

The JNJ-64619178 drug substance administered in the in vivo mouse studies and human clinical study described herein has a molecular weight of 483.37, a molecular formula of $C_{22}H_{23}BrN_6O_2$, and the chemical name of (1S,2R,3S,5R)-3-[2-(2-amino-3-bromoquinolin-7-yl)ethyl]-5-(4-amino-7H-pyrrolo[2,3-d]pyrimidin-7-yl)cyclopentane-1,2-diol. The drug substance was prepared and characterized as described in International Patent Publication No. WO-2017/032840, which is incorporated by reference herein.

Example 2. Drug Formulation

The JNJ-64619178 drug substance supplied for the clinical study described herein is formulated as 0.5 mg and 2 mg capsules for oral administration. In addition to the drug substance, each capsule includes colloidal silicon dioxide as a glidant and a hard gelatin capsule shell (size 0 for the 0.5-mg capsule and size 3 for the 2.0-mg capsule, each capsule shell comprising, e.g., gelatin and titanium dioxide).

Example 3. In Vivo Lung Cancer Models: Efficacy of JNJ-64619178 in an Established NCI-H1048 SCLC Model A. Study 1

JNJ-64619178 was tested for antitumor activity in the NCI-H1048 human xenograft model of SCLC. Male mice were subcutaneously implanted with NCI-H1048 cells, and tumors were allowed to grow for 14 days, reaching 174±51 mm$^3$ in volume, when treatment was started. Mice were administered once daily oral doses of JNJ-64619178 at 1, 3, and 10 mg/kg or 20% hydroxypropyl-β-cyclodextrin (HP-β-CD) vehicle control for up to 28 days.

Figure 2:
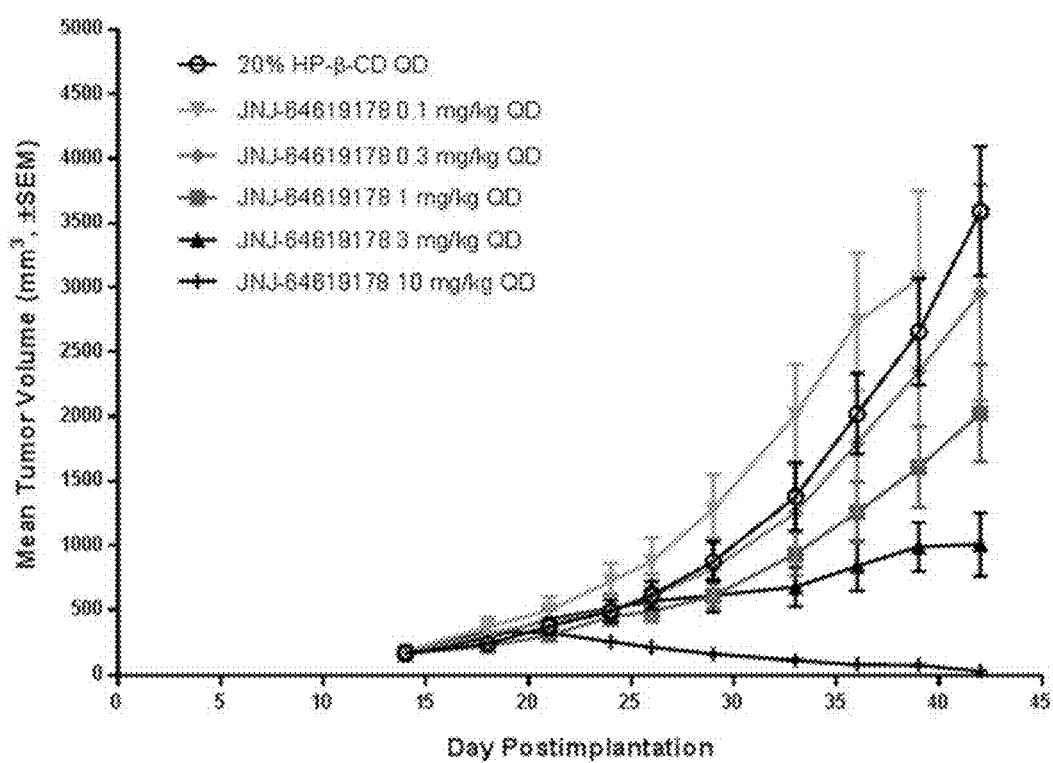
FIG. 2 is a line graph showing the prolonged pharmacodynamic modulation post-treatment of NCI-H1048 cells with the compound of the disclosure (mean tumor volume in human SCLC mouse xenograft with the compound once daily for 28 days).

JNJ-64619178 showed biologically significant antitumor activity at 3 and 10 mg/kg. At a dose of 10 mg/kg, JNJ-64619178 elicited complete regression of tumors that was maintained for up to 14 days postdose. Group mean tumor volumes are shown in FIG. 2. There was statistically significant antitumor activity at doses of 1, 3, and 10 mg/kg JNJ-64619178 compared with vehicle control, with 99.1% tumor growth inhibition (TGI) achieved with 10 mg/kg on Day 42 postimplantation.

These results were confirmed in a second human SCLC mouse xenograft study. Mice with NCI H1048 human SCLC xenografts were treated via oral gavage with JNJ-64619178 (1, 3, and 10 mg/kg) or 20% HP β CD vehicle control for 10 days, and tumor regrowth was observed for an additional 10 days. Biologically significant TGI (up to 72.9%) was observed at 10 mg/kg JNJ 64619178, which continued for several days during the postdosing period.

FIG. 1 details the individual tumor regrowth observed following cessation of once daily treatment with 10 mg/kg JNJ 64619178 or vehicle control. In all 8 mice treated with 10 mg/kg JNJ 64619178, tumor regrowth began approximately 14 days after cessation of dosing, with tumors reaching ethical limits by Day 92 postimplantation.

B. Study 2

Figure 3:
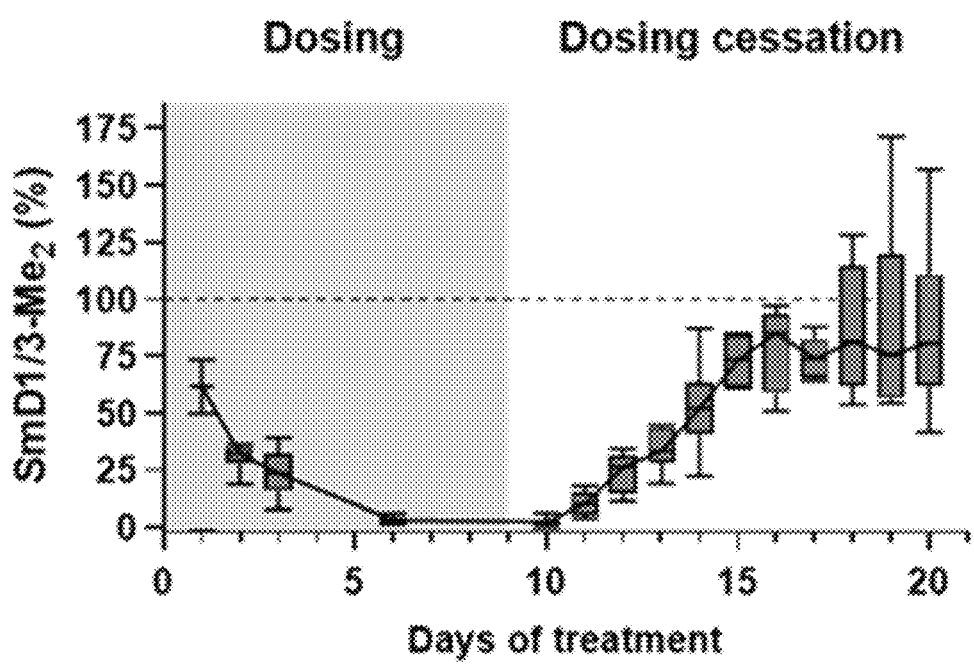
FIG. 3 is a boxplot showing SmD1/3-Me2 levels after oral dosing of NCI-H1048 lung cancer xenograft mice for 9 consecutive days with JNJ64619178 (10 mg/kg) (gray section), followed by treatment cessation for 11 days. Percentage (%) SmD1/3-Me2 levels compared to vehicle treated group (defined as 100%), was visualized as boxplots with whiskers from minimum to maximum with a line joining the median values. Dotted bar represent level of SmD1/3-Me2 in untreated samples.

NCI-H1048 lung cancer xenograft mice were orally dosed for 9 consecutive days with JNJ-64619178 (10 mg/kg), followed by treatment cessation for 11 days. At 2 h post dosing (day 0, 1, 2, 3 and 6) and every day following treatment cessation, tumors (n=3 nude mice/group) were collected and level of SmD1/3-Me2 assessed by immunoblotting and normalized to a median β-actin protein level determined from vehicle (20% HP-β-CD) treated tumor samples. The percentage (%) SmD1/3-Me2 levels compared to vehicle treated group (defined as 100%), was visualized in FIG. 3 as boxplots with whiskers from minimum to maximum with a line joining the median values. The gray shaded section represents the dosing period and the dotted bar represent level of SmD1/3-Me2 in untreated samples.

C. Study 3

Figure 4:
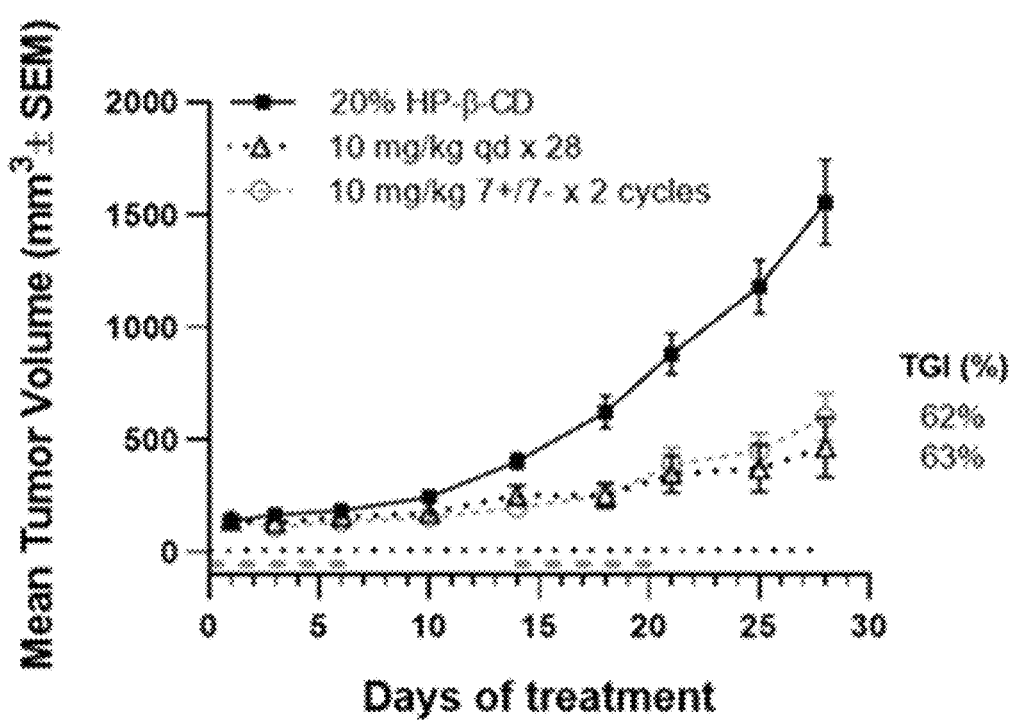
FIG. 4 is a line graph showing extended tumor growth inhibition using a dosing cessation of the compound of the disclosure in the NCI-H1048 tumor model at a JNJ64619178 dosage of 10 mg/kg for either 28 consecutive days or for two cycles of 7 daily drug treatment followed by 7 days dosing holidays (7+/7 −, 2 cycles). Tumor growth inhibition (TGI, %) compared to vehicle treatment of 62 and 63%, respectively, was calculated at day 28.

NCI-H1048 xenografts bearing mice (n=8 mice/group) were once oral daily dosed with vehicle (20% HP-β-CD) or JNJ-64619178 (10 mg/kg) for either 28 consecutive days or for two cycles of 7 daily drug treatment followed by 7 days dosing holidays (7+/7 −, 2 cycles), and tumor growth inhibition (TGI, %) compared to vehicle treatment of 62 and 63%, respectively, was calculated at d 28. In all xenografts studies, the average tumor volume at treatment initiation was about 150 mm$^3$ and mean tumor volumes (mm$^3$)±SEM of each group were graphed over time as indicated in FIG. 4.

Example 4. A Phase I Open-Label Study of the Safety, Pharmacokinetics, and Pharmacodynamics of JNJ-64619178 in Subjects with Advanced Cancers This is a multi-part, Phase 1, open-label, multicenter study to evaluate the safety, pharmacokinetics, pharmacodynamics, and preliminary clinical activity of JNJ-64619178 monotherapy administered either to adult human subjects with advanced solid tumors or B cell non-Hodgkin lymphomas who previously received or are ineligible for standard treatment options, or to adult subjects with lower risk myelodysplastic syndromes (MDS) who are red blood cell (RBC) transfusion-dependent and relapsed or refractory to erythropoiesis-stimulating agent (ESA) treatment.

Initial Clinical Results

Fifteen (15) participants with various solid tumors (e.g., breast cancer, prostate cancer, salivary duct carcinoma, adenoid cystic carcinoma) were dosed in the "Part 1" study described below with JNJ-64619178 at 0.5 mg (1' cohort), 1 mg (2$^{nd}$ cohort), 2 mg (3rd cohort) and 4 mg (4$^{th}$ cohort) under a schedule of 14 days continuous dose administration followed by a 7-day rest period (14 days on/7 days off in a 21-day cycle). Average treatment duration ranged from 4 weeks in the 4$^{th}$ cohort (4 mg 14 days on/7 days off) to 6 months in the 2$^{nd}$ cohort (1 mg 14 days on/7 days off). The most frequently reported adverse events (AEs) observed in the first 3 escalating cohorts were hematologic, gastrointestinal and dermatologic. Non-hematologic toxicities were Grade 1 or 2 except for one case of Grade 3 vomiting lasting 24 hours. No dose limiting toxicities (DLTs) were observed in the first 3 cohorts. The Part 1 study is ongoing.

Follow-on Clinical Results

Fifty-four (54) participants with various solid tumors (e.g., breast cancer, prostate cancer, salivary duct carcinoma, adenoid cystic carcinoma, and uveal melanoma) were dosed in the "Part 1" study described below with JNJ-64619178 at 0.5 mg (1$^{st}$ cohort), 1 mg (2$^{nd}$ cohort), 2 mg (3$^{rd}$ cohort), 4 mg (4$^{th}$ cohort), and 3 mg (5$^{th}$ cohort) under a schedule of 14 days continuous dose administration followed by a 7-day rest period (14 days on/7 days off in a 21-day cycle); or at 1 mg (6$^{th}$ cohort) or 2 mg (7$^{th}$ cohort) under a schedule of 21 days continuous dosing. Average treatment duration was 3 months, with a range of 0.4 to 22.4 months. Adverse events (AEs) observed in >20% of participants were gastrointestinal disorders (nausea, vomiting, diarrhea), hematologic disorders (thrombocytopenia, anemia, neutropenia), general disorders (fatigue and asthenia) and dysgeusia. Dose-limiting toxicities of thrombocytopenia of Grade 4 or of Grade 3 lasting longer than 7 days were observed in cohorts 4, 5, and 6. The maximum tolerated dose was considered 3 mg on the 14 days on/7 days off schedule or 2 mg on the continuous dosing schedule. Out of 45 participants evaluable for efficacy, 1 (4.3%), 24 (52%) and 20 (43%) had best overall response of confirmed partial response, stable disease and progressive disease, respectively. The participant with confirmed PR was from cohort 2.

JNJ64619178 plasma $C_{max}$ and AUC were linearly dose-proportional. Robust target engagement, as measured by plasma SDMA, was achieved even with intermittent dosing. A confirmed partial response (RECIST) was observed in ACC, and patients with ACC, prostate cancer, salivary gland carcinomas, and other tumor types had stable disease greater than 6 months. Two provisional RP2Ds were selected: 1.5 mg intermittently and 1 mg QD.

This data shows that JNJ64619178 demonstrated manageable toxicity and preliminary evidence of antitumor activity at selected dose levels. Intermittent dosing also maintained target inhibition.

Additional clinical testing is described below, for Part 1 and Part 2.

Clinical Protocol

Dosage and Administration

The JNJ-64619178 starting dose is based on toxicology results obtained using no observed adverse effect level (NOAEL) dose, more conservative than the highest non-severely toxic dose (HNSTD) in the dog as the most sensitive species. Using a default safety factor of 6 (used for HNSTD in non-rodents), a starting dose of 0.54 mg once daily (QD) was obtained, which was rounded to 0.5 mg QD. A single dose of the study drug will be administered in the

TABLE A

OBJECTIVES, ENDPOINTS, AND HYPOTHESES

| Objectives | Endpoints |
|---|---|
| *Primary* | |
| Part 1 To identify the MTD of JNJ-64619178 in subjects with relapsed/refractory B cell non-Hodgkin lymphoma (NHL) or advanced solid tumors To identify the RP2D(s) of JNJ-64619178 for NHL and advanced solid tumors | Frequency, type, and severity of dose-limiting toxicity (DLT) observed |
| Part 2 To confirm the tolerability of JNJ-64619178 in subjects with lower risk MDS | Frequency, type, and severity of toxicities |
| *Secondary* | |
| To characterize the safety of JNJ-64619178 (Part 1 & 2) | Safety profile of JNJ-64619178 (safety parameters include but are not limited to the frequency and severity of adverse events, as well as abnormal vital signs, clinical laboratory values, and ECGs) |
| To characterize the pharmacokinetics of JNJ-64619178 (Part 1 & 2) | Plasma concentration-time profiles and pharmacokinetic parameters for JNJ-64619178 including but not limited to $C_{max}$, $AUC_t$, $C_{min}$, $T_{1/2}$, Vss/F, CL/F, and $R_A$ |
| To characterize the pharmacodynamics of JNJ-64619178 (Part 1 & 2) | Plasma concentration of symmetric dimethyl-arginine (SDMA) |
| To evaluate the preliminary clinical activity of JNJ-64619178 in subjects with relapsed/refractory B cell NHL or advanced solid tumors (Part 1) | Objective response rate, duration of response, and clinical benefit response rate Response for lymphoma will be assessed according to Lugano Classification Response for solid tumors will be assessed according to the Response Evaluation Criteria in Solid Tumors (RECIST) v1.1 |
| To evaluate the preliminary clinical activity of JNJ-64619178 in subjects with lower risk MDS (Part 2) | RBC transfusion independence (TI) rate and overall improvement rate (complete remission, partial remission, and hematologic improvement) according to the modified International Working Group (IWG) response criteria |
| *Exploratory* | |
| To assess time to response To explore the relationships between pharmacokinetics, pharmacodynamics, and exploratory biomarkers (eg, protein/DNA/RNA analysis), adverse event profiles, and clinical activity or resistance to JNJ-64619178 To characterize effects of JNJ-64619178 on myeloid cell differentiation | |

Subject Population

For purposes of this example, eligible subjects must be ≥18 years of age with relapsed or refractory B cell NHL (diffuse large B cell lymphoma, follicular lymphoma, or mantle cell lymphoma), RBC-transfusion-dependent and ESA-relapsed or refractory lower risk MDS, or advanced or refractory solid tumors, histological documentation of disease, at least 1 measurable site of disease for solid tumors and NHL, an Eastern Cooperative Oncology Group (ECOG) performance status score of Grade 0 or 1, and laboratory values and cardiac parameters within the study specified criteria for enrollment.

pharmacokinetic run-in phase for Part 1. During the treatment phase, the study drug will be administered for 14 consecutive days followed by 7 days of rest (14 days on/7 days off dose administration) on a 21 day cycle. Alternative dosing schedules (e.g., continuous dosing, 7 days on/7 days off, and 7 days on/14 days off) are also evaluated.

The study was initiated with dose Schedule A (14 days on/7 days off dose administration on a 21-day cycle). Table B below provides an example of possible dose escalation. An overview of the study drug administration is provided in Table C.

TABLE B

Planned Dose Escalation Schedule for Part 1

| Dose Level | Proposed dose level[a] | Maximum increment from previous dose |
|---|---|---|
| 1 | 0.5 mg | Starting dose |
| 2 | 1.0 mg | 100% |
| 3 | 2.0 mg | 100% |
| 4 | 4.0 mg | 100% |
| 5 | 8.0 mg | 100% |
| 6 | 12.0 mg | 50% |
| 7 | 16.0 mg | 33% |
| 8 | 20.0 mg | 25% |

[a]Intermediate doses may be considered based on SET assessment.

TABLE C

| Description of Study Drug - JNJ-64619178 Administration | |
|---|---|
| Study Drug | JNJ-64619178 |
| Dosage formulation/Unit dose strength(s) | Capsule will be supplied as 0.5 mg and 2 mg strengths |
| Starting dose/dose levels | Dose escalation will be initiated at a starting dose of 0.5 mg. |
| Route of administration | Oral |
| Frequency | Continuous once daily (QD) dose administration |
| Starting Schedule | Schedule A. See Table D. |
| Alternative Schedules | Schedules B, C, D; see Table D. |
| Dose administration instructions | Capsules for at-home use. Capsules must be taken fasting. The first dose of study drug will be administered at the site followed by a 6-day rest period (i.e., pharmacokinetic run-in period). Study drug will resume on Cycle 1 Day 1 if no DLTs are reported. Subjects in Part 2 will not have the PK run-in period. |

Study drug administration schedules are presented in Table D:

TABLE D

| | Study Day | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| Schedule A (14 Days on/7 Days off dose administration on a 21-day cycle) | | | | | | | | | | | | | | | | | | | | | |
| Study Drug | x | x | x | x | x | x | x | x | x | x | x | x | x | x | — | — | — | — | — | — | — |
| Schedule B (Continuous daily dose administration on a 21-day cycle) | | | | | | | | | | | | | | | | | | | | | |
| Study Drug | x | x | x | x | x | x | x | x | x | x | x | x | x | x | x | x | x | x | x | x | x |
| Schedule C (7 Days on/14 Days off dose administration on a 21-day cycle) | | | | | | | | | | | | | | | | | | | | | |
| Study Drug | x | x | x | x | x | x | x | — | — | — | — | — | — | — | — | — | — | — | — | — | — |

| | Schedule D (7 Days on/7 Days off dose administration on a 21-day cycle) | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | Study Day | | | | | | | | | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
| Study Drug | x | x | x | x | x | x | x | — | — | — | — | — | — | — | x | x | x | x | x | x | x | — | — | — | — | — | — | — |

The study is divided into 2 parts that have up to 4 periods: a screening phase, a pharmacokinetic run-in phase, a treatment phase, and a posttreatment follow-up phase. Study drug administration schedules are presented in Table D above.

Pharmacokinetic Run-in Phase

The pharmacokinetic run-in phase will evaluate the single-dose pharmacokinetics of JNJ 64619178 prior to subsequent daily dose administration in the treatment phase. Subjects will be administered a single-dose of study drug at the site on Day 1 and remain at site for at least 6 hours for pharmacokinetic assessments. The single-dose of study drug will be followed by a 6 day rest period (i.e., Days 2 to 7 [a range of 5 to 10 days is allowed]) during which pharmacokinetic blood sample and ECG collection will be conducted. Certain subjects in Part 1 may not participate in the pharmacokinetic run-in phase.

Treatment Phase

The treatment phase begins on Cycle 1 Day 1 with the administration of the study drug and continues until the completion of the end-of-treatment visit. During the treatment phase, multiple-dose pharmacokinetics of JNJ-64619178 will be evaluated. On Cycle 1 Day 14, subjects in Part 1 will remain at site for at least 8 hours after the study drug administration for pharmacokinetic and ECG assessments. Study drug should be administered at approximately the same time each day for accurate evaluation of the pharmacokinetics of JNJ 64619178.

Subjects will come to the site on Day 1 of each cycle for study drug administration and to receive enough study drug for self-administration at home. A diary card will be provided to record study drug intake at home. Instructions for self-administration at home will be reinforced at each visit. At each clinic visit, the subject will also be evaluated for possible toxicities.

The study drug may be administered until disease progression (according to disease-specific criteria), or until any of the study drug discontinuation criteria are met. Subjects in Part 2 will receive treatment for a minimum of 24 weeks unless they meet criteria for study drug discontinuation earlier. Subjects with evidence of clinical benefit may continue on study drug until disease progression or loss of hematologic response. Upon discontinuation of the study drug, the subject will complete an end-of-treatment visit.

Adverse Event Reporting (i) Adverse Event: An adverse event is any untoward medical occurrence in a clinical study subject administered a medicinal (investigational or non-investigational) product. An adverse event does not necessarily have a causal relationship with the study drug. An adverse event can therefore be any unfavorable and unintended sign (including an abnormal finding), symptom, or disease temporally associated with the use of a medicinal (investigational or non-investigational) product, whether or not related to that medicinal (investigational or non-investigational) product. (Definition per International Conference on Harmonisation [ICH]). This includes any occurrence that is new in onset or aggravated in severity or frequency from the baseline condition, or abnormal results of diagnostic procedures, including laboratory test abnormalities.

(ii) Serious Adverse Event: A serious adverse event based on ICH and EU Guidelines on Pharmacovigilance for Medicinal Products for Human Use is any untoward medical occurrence that at any dose:
Results in death
Is life-threatening
(The subject was at risk of death at the time of the event. It does not refer to an event that hypothetically might have caused death if it were more severe.)
Requires inpatient hospitalization or prolongation of existing hospitalization
Results in persistent or significant disability/incapacity
Is a congenital anomaly/birth defect
Is a suspected transmission of any infectious agent via a medicinal product
Is Medically Important*
*Medical and scientific judgment should be exercised in deciding whether expedited reporting is also appropriate in other situations, such as important medical events that may not be immediately life threatening or result in death or hospitalization but may jeopardize the subject or may require intervention to prevent one of the other outcomes listed in the definition above. These should usually be considered serious.

Unlisted (Unexpected) Adverse Event/Reference Safety Information

An adverse event is considered unlisted if the nature or severity is not consistent with the applicable product reference safety information.

Adverse Event Associated With the Use of the Study Drug

An adverse event is considered associated with the use of the study drug if the attribution is possible, probable, or very likely.

(iii) Attribution Definitions

Not Related: An adverse event that is not related to the use of the study drug.

Doubtful: An adverse event for which an alternative explanation is more likely, e.g., concomitant drug(s), concomitant disease(s), or the relationship in time suggests that a causal relationship is unlikely.

Possible: An adverse event that might be due to the use of the study drug. An alternative explanation, e.g., concomitant drug(s), concomitant disease(s), is inconclusive. The relationship in time is reasonable; therefore, the causal relationship cannot be excluded.

Probable: An adverse event that might be due to the use of the study drug. The relationship in time is suggestive (e.g., confirmed by dechallenge). An alternative explanation is less likely, e.g., concomitant drug(s), concomitant disease(s).

Very Likely: An adverse event that is listed as a possible adverse reaction and cannot be reasonably explained by an alternative explanation, e.g., concomitant drug(s), concomitant disease(s). The relationship in time is very suggestive (e.g., it is confirmed by dechallenge and rechallenge).

(iv) Severity Criteria

An assessment of severity grade will be made according to the NCI CTCAE Version 4.03. See Table E.

TABLE E

| | Activities of Daily Living (ADL) |
|---|---|
| Grade 1 | Mild; asymptomatic or mild symptoms; clinical or diagnostic observations only; intervention not indicated. |
| Grade 2 | Moderate; minimal, local or noninvasive intervention indicated; limiting age-appropriate instrumental activities of daily living.* |

TABLE E-continued

Activities of Daily Living (ADL)

| | |
|---|---|
| Grade 3 | Severe or medically significant but not immediately life-threatening; hospitalization or prolongation of hospitalization indicated; disabling; limiting self-care activities of daily living.** |
| Grade 4 | Life-threatening consequences; urgent intervention indicated. |
| Grade 5 | Death related to adverse event. |

*Instrumental ADL refer to preparing meals, shopping for groceries or clothes, using the telephone, managing money, etc.
**Self-care ADL refer to bathing, dressing and undressing, feeding self, using the toilet, taking medications, and not bedridden.

What is claimed is:

1. A method for treating a human patient diagnosed with a cancer, comprising administering a therapeutically effective amount of a PRMT5 (protein arginine methyltransferase 5) inhibitor, the method comprising:
   (i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 7 days to about 14 days;
   (ii) after the initial period, administering to the patient no doses of the PRMT5 inhibitor for an off-period of about 7 days to about 14 days;
   (iii) after the off-period, administering to the patient subsequent doses of at least about 0.1 mg per day of the PRMT5 inhibitor for a subsequent dosing period of about 7 days to about 14 days;
   (iv) after the subsequent dosing period, administering to the patient no doses of the compound for an off-period of about 7 days to about 14 days; and
   (v) sequentially repeating steps (iii) and (iv) at least 4 times.

2. The method of claim 1, comprising:
   (i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 14 days;
   (ii) after the initial period, administering to the patient no doses of the PRMT5 inhibitor for an off-period of about 7 days;
   (iii) after the off-period, administering to the patient subsequent doses of at least about 0.1 mg per day of the PRMT5 inhibitor for a subsequent dosing period of about 14 days; and
   (iv) after the subsequent dosing period, administering to the patient no doses of the compound for an off-period of about 7 days.

3. The method of claim 1, comprising:
   (i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 7 days;
   (ii) after the initial period, administering to the patient no doses of the PRMT5 inhibitor for an off-period of about 7 days;
   (iii) after the off-period, administering to the patient subsequent doses of at least about 0.1 mg per day of the PRMT5 inhibitor for a subsequent dosing period of about 7 days; and
   (iv) after the subsequent dosing period, administering to the patient no doses of the compound for an off-period of about 7 days.

4. The method of claim 1, comprising:
   (i) administering to the patient initial doses of at least about 0.1 mg per day of the PRMT5 inhibitor that is (1S,2R,3S,5R)-3-(2-(2-amino-3-bromoquinolin-7-yl) ethyl)-5-(4-amino-7H-pyrrolo[2,3-d]pyrimidin-7-yl) cyclopentane-1,2-diol or a pharmaceutically acceptable addition salt or solvate thereof for an initial dosing period of about 7 days;
   (ii) after the initial period, administering to the patient no doses of the PRMT5 inhibitor for an off-period of about 7 days;
   (iii) after the off-period, administering to the patient subsequent doses of at least about 0.1 mg per day of the PRMT5 inhibitor for a subsequent dosing period of about 14 days; and
   (iv) after the subsequent dosing period, administering to the patient no doses of the compound for an off-period of about 7 days.

5. The method of claim 1, comprising administering to the patient the initial doses of about 0.5 mg to about 5 mg per day of the PRMT5 inhibitor and administering to the patient the subsequent doses of about 0.5 mg to about 5 mg per day of the PRMT5 inhibitor.

6. The method of claim 1, wherein the cancer is characterized by a splicing factor mutation.

7. The method of claim 1, wherein each of the initial dose per day or subsequent dose per day is, independently, at least about 0.5 mg, at least about 1 mg, at least 1.5 mg, at least about 2 mg, at least about 3 mg, at least about 4 mg, at least about 5 mg, at least about 5.5 mg, at least about 6 mg, at least about 8 mg, at least about 16 mg, at least about 30 mg, or at least about 60 mg.

8. The method of claim 1, wherein each of the initial dose per day or subsequent dose per day is, independently, about 0.1 to about 100 mg, about 0.5 to about 80 mg, about 0.5 to about 60 mg, 0.5 to about 30 mg, about 0.5 to about 16 mg, about 0.5 to about 8 mg, about 0.5 to about 4 mg, about 0.5 to about 2 mg, or about 0.5 to about 1 mg.

9. The method of claim 1, wherein each of the initial dose per day and subsequent dose per day is, independently, about 0.5 mg, about 1 mg, about 1.5 mg, about 2 mg, about 3 mg, about 4 mg, about 5 mg, about 5.5 mg, about 6 mg, about 8 mg, about 12.5 mg, about 16 mg, about 25 mg, about 30 mg, about 50 mg, about 60 mg, about 100 mg, about 200 mg, about 400 mg, about 600 mg, about 800 mg, or about 1200 mg.

10. The method of claim 1, wherein each of the initial dose or at least one subsequent dose is administered once daily or both the initial dose and at least one subsequent dose are administered once daily.

11. The method of claim 1, wherein each of the initial dose or at least one subsequent dose is administered in divided doses or both the initial dose and at least one subsequent dose are administered in divided doses.

12. The method of claim 11, wherein the divided doses are equal.

13. The method of claim 11, wherein one or both divided dose is twice daily (BID).

14. The method of claim 1, wherein the initial dosing period is about 7 days to about 14 days.

15. The method of claim 1, wherein the initial dosing period is about 7 days.

16. The method of claim 1, wherein the initial dosing period is about 14 days.

17. The method of claim 1, wherein the first subsequent dosing period is separated in time from the initial dosing period by at least about 7 days; and the subsequent dosing periods are separated in time from each other by at least about 7 days.

18. The method of claim 1, wherein the first subsequent dosing period is separated in time from the initial dosing period by about 7 days; and the subsequent dosing periods are separated in time from each other by about 7 days.

19. The method of claim 1, wherein each subsequent dosing period is about 7 days to about 14 days.

20. The method of claim 1, wherein each subsequent dosing period is about 7 days.

21. The method of claim 1, wherein the first subsequent dosing period is separated in time from the initial dosing period by at least about 14 days; and the subsequent dosing periods are separated in time from each other by at least about 14 days.

22. The method of claim 1, wherein each subsequent dosing period is about 14 days.

23. The method of claim 1, wherein the initial dose or at least one subsequent dose is administered orally or the initial dose and at least one subsequent dose are administered orally.

24. The method of claim 1, wherein the initial dose or at least one subsequent dose is administered parenterally or the initial dose and at least one subsequent dose are administered parenterally.

25. The method of claim 1, wherein the initial dose and at least one subsequent dose are the same.

26. The method of claim 1, wherein the initial dose and at least one subsequent dose are different.

27. The method of claim 1, wherein the cancer is an advanced cancer.

28. The method of claim 1, wherein the cancer is acoustic neuroma, adenocarcinoma, adenoid cystic carcinoma, adrenal gland cancer, anal cancer, angiosarcoma, appendix cancer, benign monoclonal gammopathy, biliary cancer, bladder cancer, breast cancer, brain cancer, bronchus cancer, carcinoid tumor, cervical cancer, chordoma, choriocarcinoma, craniopharyngioma, colorectal cancer, epithelial carcinoma, ependymoma, endothelio sarcoma, endometrial cancer, esophageal cancer, Ewing sarcoma, eye cancer, familiar hypereosinophilia, gall bladder cancer, gastric cancer, gastrointestinal stromal tumor, head and neck cancer, hematopoietic cancer, heavy chain disease, hemangioblastoma, inflammatory myofibroblastic tumor, immunocytic amyloidosis, kidney cancer, liver cancer, lung cancer, leiomyosarcoma, mastocytosis, myelodysplastic syndrome, mesothelioma, myeloproliferative disorder, neuroblastoma, neurofibroma, neuroendocrine cancer, osteosarcoma, ovarian cancer, papillary adenocarcinoma, pancreatic cancer, penile cancer, pinealoma, primitive neuroectodermal tumor, prostate cancer, rectal cancer, rhabdomyosarcoma, salivary gland cancer, skin cancer, small bowel cancer, soft tissue sarcoma, sebaceous gland carcinoma, sweat gland carcinoma, synovioma, testicular cancer, thyroid cancer, urethral cancer, uveal melanoma, vaginal cancer, or vulvar cancer.

29. The method of claim 1, wherein the cancer is a solid tumor cancer.

30. The method of claim 1, wherein the cancer is a non-small cell lung cancer.

31. The method of claim 1, wherein the cancer is a hematopoietic cancer.

32. The method of claim 31, wherein the cancer is non-Hodgkin's lymphoma, Hodgkin's lymphoma, myeloma, CMML, MDS or AML.

33. The method of claim 1, further comprising administering an adjuvant therapy to the patient.

34. The method of claim 33, wherein the adjuvant therapy comprises administering radiation to the patient.

35. The method of claim 33, wherein the adjuvant therapy comprises administering an effective amount of a chemotherapeutic agent to the patient.

36. The method of claim 35, wherein the chemotherapeutic agent is a DNA methyl transferase inhibitor.

37. The method of claim 36, wherein the DNA methyl transferase inhibitor is 5-azacitidine or decitabine.

38. The method of claim 1, wherein efficacy is measured by determining a patient time to disease progression or a patient response rate.

39. The method of claim 1, wherein the compound is a pharmaceutically acceptable addition salt of (1S,2R,3S,5R)-3-(2-(2-amino-3-bromoquinolin-7-yl)ethyl)-5-(4-amino-7H-pyrrolo[2,3-d]pyrimidin-7-yl)cyclopentane-1,2-diol.

40. The method of claim 1, wherein the compound is a solvate of (1S,2R,3S,5R)-3-(2-(2-amino-3-bromoquinolin-7-yl)ethyl)-5-(4-amino-7H-pyrrolo[2,3-d] pyrimidin-7-yl) cyclopentane-1,2-diol.

41. The method of claim 40, wherein the solvate is a hydrate.

42. The method of claim 1, wherein the compound is (1S,2R,3S,5R)-3-(2-(2-amino-3-bromoquinolin-7-yl)ethyl)-5-(4-amino-7H-pyrrolo[2,3-d] pyrimidin-7-yl)cyclopentane-1,2-diol.

* * * * *